US008555891B2

(12) United States Patent
Sharkawy et al.

(10) Patent No.: US 8,555,891 B2
(45) Date of Patent: Oct. 15, 2013

(54) IMPLANT SYSTEM FOR CONTROLLING AIRWAY PASSAGE

(75) Inventors: Adam Sharkawy, San Jose, CA (US); Koray Sahin, Santa Clara, CA (US); Adrian McVicker, Sunnyvale, CA (US); Jon F. Moss, Antioch, CA (US); Casidy Domingo, San Mateo, CA (US); Nikhil D. Bhat, Fremont, CA (US); Christopher Bagley, Santa Clara, CA (US); Anant V. Hegde, Hayward, CA (US); John M. Farbarik, Castro Valley, CA (US); George Y. Choi, Redwood City, CA (US); Kasey Kai-Chi Li, Palo Alto, CA (US)

(73) Assignee: Medtronic Xomed, Inc., Jacksonville, FL (US)

( * ) Notice: Subject to any disclaimer, the term of this patent is extended or adjusted under 35 U.S.C. 154(b) by 213 days.

(21) Appl. No.: 12/785,391

(22) Filed: May 21, 2010

(65) Prior Publication Data

US 2010/0319710 A1 Dec. 23, 2010

Related U.S. Application Data

(63) Continuation-in-part of application No. PCT/US2010/024604, filed on Feb. 18, 2010.

(60) Provisional application No. 61/153,455, filed on Feb. 18, 2009, provisional application No. 61/305,934, filed on Feb. 18, 2010, provisional application No. 61/182,041, filed on May 28, 2009.

(51) Int. Cl.
*A61F 5/56* (2006.01)
*A61B 1/32* (2006.01)

(52) U.S. Cl.
USPC ............................ 128/848; 600/235; 600/237

(58) Field of Classification Search
USPC ........... 128/848, 846, 845; 602/902; 433/140; 606/60, 90, 105; 600/201, 202, 235, 600/237, 240
See application file for complete search history.

(56) References Cited

U.S. PATENT DOCUMENTS

| | | | |
|---|---|---|---|
| 4,838,283 | A | 6/1989 | Lee, Jr. |
| 5,078,153 | A | 1/1992 | Nordlander et al. |
| 5,176,618 | A | 1/1993 | Freedman |

(Continued)

FOREIGN PATENT DOCUMENTS

| | | | |
|---|---|---|---|
| EP | 0 743 076 | A1 | 11/1996 |
| EP | 1 110 518 | A1 | 6/2001 |
| WO | 99/00058 | A1 | 1/1999 |
| WO | 2008/079700 | A2 | 7/2008 |

*Primary Examiner* — Victoria J Hicks
(74) *Attorney, Agent, or Firm* — Dicke, Billig & Czaja, PLLC

(57) ABSTRACT

Techniques for operating a subcutaneous implant device are disclosed. The implant device can be formed of a non-magnetic material that is compatible with diagnostics such as magnetic resonance imaging (MRI) and can include a rotor element that rotates under the influence of an external magnetic field. The implant device includes a tension relief mechanism for relieving excessive force applied between the implant device and a portion of a patient's tongue. A non-implanted device can include a stator and drive circuitry for generating the external magnetic field. The non-implanted device can receive a user command and can vary the external magnetic field based on the command. When activated by the magnetic field, the implant device can change its operating state to interact with the patient's body.

20 Claims, 20 Drawing Sheets

100
110
120
130
140

(56) References Cited

U.S. PATENT DOCUMENTS

| | | | | |
|---|---|---|---|---|
| 5,979,456 | A | 11/1999 | Magovern | |
| 6,516,806 | B2 | 2/2003 | Knudson et al. | |
| 6,955,172 | B2 | 10/2005 | Nelson et al. | |
| 7,073,505 | B2 | 7/2006 | Nelson et al. | |
| 7,188,627 | B2 | 3/2007 | Nelson et al. | |
| 7,213,599 | B2 | 5/2007 | Conrad et al. | |
| 7,216,648 | B2 | 5/2007 | Nelson et al. | |
| 7,237,554 | B2 | 7/2007 | Conrad et al. | |
| 7,360,542 | B2 | 4/2008 | Nelson et al. | |
| 7,367,340 | B2 | 5/2008 | Nelson et al. | |
| 8,096,303 | B2 * | 1/2012 | Dineen et al. | 128/848 |
| 2005/0159637 | A9 | 7/2005 | Nelson et al. | |
| 2006/0235264 | A1 * | 10/2006 | Vassallo | 600/37 |
| 2007/0186936 | A1 | 8/2007 | Nelson et al. | |
| 2008/0023012 | A1 | 1/2008 | Dineen et al. | |
| 2008/0058584 | A1 | 3/2008 | Hirotsuka et al. | |
| 2008/0066764 | A1 * | 3/2008 | Paraschac et al. | 128/848 |
| 2008/0066765 | A1 | 3/2008 | Paraschac et al. | |
| 2008/0066766 | A1 | 3/2008 | Paraschac et al. | |
| 2008/0066767 | A1 | 3/2008 | Paraschac et al. | |
| 2008/0066769 | A1 | 3/2008 | Dineen et al. | |
| 2009/0025734 | A1 | 1/2009 | Doelling et al. | |

* cited by examiner

IMPLANT SYSTEM FOR CONTROLLING AIRWAY PASSAGE

CROSS-REFERENCES TO RELATED APPLICATIONS

This application is a continuation-in-part of International Application No. PCT/US10/024,604, filed on Feb. 18, 2010, which claims the benefit of U.S. Provisional Application No. 61/153,455, filed Feb. 18, 2009, and this application also claims the benefit of U.S. Provisional Application No. 61/305,934, filed Feb. 18, 2010, and this application also claims the benefit of U.S. Provisional Application No. 61/182,041, filed May 28, 2009, the entireties of all being incorporated by reference herein for all purposes.

BACKGROUND OF THE INVENTION

The present invention relates generally to medical devices and, more particularly, to operating an implant.

Snoring is a noise produced while breathing during sleep due to the vibration of the soft palate and uvula. Snoring is very common among humans and not all snoring is bad. However, snoring may worsen over time and, if left untreated, could lead to apnea.

Those with apnea stop breathing in their sleep, often hundreds of times during the night. Usually apnea occurs when the throat muscles and tongue relax during sleep and partially block the opening of the airway. When the muscles of the soft palate at the base of the tongue and the uvula relax and sag, the airway can become blocked, making breathing labored and noisy and even stopping it altogether. Sleep apnea also can occur in obese people when an excess amount of tissue in the airway causes it to be narrowed.

In a given night, the number of involuntary breathing pauses or "apneic events" may be as high as 20 to 60 or more per hour. These breathing pauses are almost always accompanied by snoring between apnea episodes. Sleep apnea can also be characterized by choking sensations.

Sleep apnea is diagnosed and treated by primary care physicians, pulmonologists, neurologists, or other physicians with specialized training in sleep disorders. Diagnosis of sleep apnea is not simple because there can be many different reasons for disturbed sleep.

The specific therapy for sleep apnea is tailored to the individual patient based on medical history, physical examination, and the results of polysomnography. Medications are generally not effective in the treatment of sleep apnea. Oxygen is sometimes used in patients with central apnea caused by heart failure, but is not used to treat obstructive sleep apnea.

Continuous positive airway pressure (CPAP) is the most common treatment for sleep apnea. In this procedure, the patient wears a mask over the nose or mouth during sleep, and pressure from an air blower forces air through the air passages. The air pressure is adjusted so that it is just enough to prevent the throat from collapsing during sleep. The pressure is constant and continuous. CPAP prevents airway closure while in use, but apnea episodes return when CPAP is stopped or it is used improperly.

Many variations of CPAP devices are available. All have the same side effects such as nasal irritation and drying, facial skin irritation, abdominal bloating, mask leaks, sore eyes, and headaches. Some versions of CPAP devices vary the pressure to coincide with the person's breathing pattern, and other CPAP devices start with low pressure and slowly increase it to allow the person to fall asleep before the full prescribed pressure is applied.

Dental appliances that reposition the lower jaw and the tongue have been helpful to some patients with mild to moderate sleep apnea and those who snore but do not have apnea. A dentist or orthodontist can customize such a device to fit the patient.

Some patients with sleep apnea may need surgery. Although several surgical procedures are used to increase the size of the airway, none is completely successful or without risks. More than one procedure may need to be tried before the patient realizes any benefits. Some of the more common procedures include removal of adenoids and tonsils (especially in children), nasal polyps or other growths, or other tissue in the airway and correction of structural deformities. Younger patients seem to benefit from these surgical procedures more than older patients.

Uvulopalatopharyngoplasty (UPPP) is a procedure used to remove excess tissue at the back of the throat (tonsils, uvula, and part of the soft palate). The success of this technique may range from 30 to 60 percent. The long-term side effects and benefits are not known, and it is difficult to predict which patients will do well with this procedure.

Laser-assisted uvulopalatoplasty (LAUP) is done to eliminate snoring but has not been shown to be effective in treating sleep apnea. This procedure involves using a laser device to eliminate tissue in the back of the throat. Like UPPP, LAUP may decrease or eliminate snoring but not eliminate sleep apnea. Elimination of snoring, the primary symptom of sleep apnea, without influencing the condition may carry the risk of delaying the diagnosis and possible treatment of sleep apnea in patients who elect to have LAUP. To identify possible underlying sleep apnea, sleep studies are usually required before LAUP is performed.

Somnoplasty is a procedure that uses RF to reduce the size of some airway structures such as the uvula and the back of the tongue. This technique helps in reducing snoring and is being investigated as a treatment for apnea.

Tracheostomy is used in persons with severe, life-threatening sleep apnea. In this procedure, a small hole is made in the windpipe and a tube is inserted into the opening. This tube stays closed during waking hours and the person breathes and speaks normally. It is opened for sleep so that air flows directly into the lungs, bypassing any upper airway obstruction. Although this procedure is highly effective, it is an extreme measure that is rarely used.

Patients in whom sleep apnea is caused by deformities of the lower jaw may benefit from surgical reconstruction. Surgical procedures to treat obesity are sometimes recommended for sleep apnea patients who are morbidly obese. Behavioral changes are an important part of the treatment program and, in mild cases, behavioral therapy may be all that is needed. Overweight persons can benefit from losing weight. Even a 10 percent weight loss can reduce the number of apneic events for most patients.

Individuals with apnea should avoid the use of alcohol and sleeping pills, which make the airway more likely to collapse during sleep and prolong the apneic periods. In some patients with mild sleep apnea, breathing pauses occur only when they sleep on their backs. In such cases, using pillows and other devices that help them sleep in a side position may be helpful.

Recently, Restore Medical, Inc., Saint Paul, Minn. has developed a new treatment for snoring and apnea, called the Pillar technique. The Pillar System involves a procedure where three or more small polyester rod devices are placed in the patient's soft palate. The Pillar System stiffens the palate, reduces vibration of the tissue, and prevents the possible airway collapse. Stiff implants in the soft palate, however, could hinder patient's normal functions like speech, ability to swallow, coughing and sneezing. Protrusion of the implant into the airway is another long-term concern.

As the current treatments for snoring and/or apnea may not be effective and have side-effects, there is a need for additional treatment options.

BRIEF SUMMARY OF THE INVENTION

One embodiment of the invention provides an implantable device for stabilizing a tongue. The implantable device may include a mandibular anchor. An actuator mechanism may be securable to the mandibular anchor. A tongue anchor may be anchorable to the base of the tongue. A linking section may join the actuator mechanism to the tongue anchor. The linking section may be adapted to exert a pulling force on the tongue anchor in response to an operation of the actuator mechanism. A tension relief mechanism may be adapted to permit a movement of the linking section relative to the actuator mechanism when a force between the mandibular anchor and the tongue anchor exceeds a threshold value.

In one aspect of the implantable device, the actuator mechanism may include a rotor coupled to a shaft, and the pulling force of the actuator mechanism may be based on a rotation of the rotor.

In another aspect of the implantable device, the rotor may be adapted to rotate under the influence of a electromagnetic field external to the implantable device.

In another aspect of the implantable device, the actuator mechanism further may include a gearbox having an input coupled to the shaft and an output coupled to the linking section.

In another aspect of the implantable device, the gearbox may be one of a planetary gearbox, spur gear train, work gear, hydraulic pump, pneumatic pump, friction clutch, screw mechanism, spring mechanism, compressed ball bearing mechanism, and pulley system adapted so as to provide the output at a reduced a rotational speed relative to a rotational speed of the shaft.

In another aspect of the implantable device, a spool may be coupled to the output of the gearbox, and the linking section may include a tether coupled to the spool at one end and to the tongue anchor at another end.

In another aspect of the implantable device, in the linking portion may include a rigid structure.

In another aspect of the implantable device, the tension relief mechanism may include a spring.

In another aspect of the implantable device, the linking portion may be flexible in relation to a tension of the spring.

In another aspect of the implantable device, the spring may begin to elongate when the force between the mandibular anchor and the tongue anchor exceeds the threshold value.

In another aspect of the implantable device, the spring may form part of or may be in series with the linking section between the actuator mechanism and the tongue anchor.

In another aspect of the implantable device, the spring may be a closed coil spring.

In another aspect of the implantable device, the tension relief mechanism may include a compression element captured between tension members.

In another aspect of the implantable device, a second tongue anchor is provided, and the linking section may include a first tether and a second tether each coupled at one end to the actuator mechanism and to a respective one of the tongue anchors at another end.

In another aspect of the implantable device, a location of the second anchor may be different than a location of the first anchor.

In another aspect of the implantable device, the pulling force may be less than 10 N and the threshold force value may be greater than 1 N.

In another aspect of the implantable device, the pulling force may be in the range of 2-5 N and the threshold force value may be greater than 2 N.

In another aspect of the implantable device, the tongue anchor can include a tension spring configured to partially or fully elongate when below the threshold value.

In another aspect of the implantable device, the tension spring may be configured to screw into the base of the tongue.

In another aspect of the implantable device, the tension spring may be connected to a plurality of resilient anchoring members.

Another embodiment of the invention provides a method of stabilizing a tongue with an implantable device adapted for insertion into a patient's body in the vicinity of the mandibula. An electromagnetic field may be received at a rotor of the implantable device. A stabilization force may be developed when the rotor rotates under the influence of the electromagnetic field. The stabilization force may be communicated to the tongue via a tether. The stabilization force may be released when a total force on the tether exceeds a threshold value.

In one aspect of the method, the stabilization force may be restored when the total force on the tether does not exceed the threshold value.

In another aspect of the method, developing the stabilization force may include using a gearbox to increase a torque generated by rotation of the rotor.

In another aspect of the method, communicating the stabilization force may include laterally displacing the tether.

In another aspect of the method, the tether may be laterally displaced along a transverse axis of the implantable device.

In another aspect of the method, the tether may be guided along a transverse axis of the implantable device.

In another aspect of the method, releasing the stabilization force may include elongating a spring of the implantable device.

In another aspect of the method, the stabilization force may include disengaging a clutch mechanism of the implantable device.

In another aspect of the method, the total force on the tether may include a sum of the stabilization force and an external force.

In another aspect of the method, communicating the stabilization force may include applying a tension between the mandibula and the tongue.

Another embodiment of the invention provides another implantable device for stabilizing a tongue. The device may include a means for securing a first part of the implantable device to a patient's mandibula. The device may also include a means for securing a second part of the implantable device to the patient's tongue. The device may also include a means for developing a stabilization force in response to an electromagnetic field received from a source external to the implantable device. The device may also include a means for communicating the stabilization force to the patient's tongue. The device may also include a means for releasing the stabilization force when a force between the patient's mandibula and the patient's tongue carried by the implantable device exceeds a predetermined threshold value.

Another embodiment of the invention provides another implantable device for stabilizing a tongue. The implantable device may include a mandibular anchor. An actuator mechanism may be coupled to the mandibular anchor. The actuator device may include a rotor disposed within a housing of the actuator mechanism and adapted to rotate under the influence of an external electromagnetic field. A shaft may be coupled to the rotor. A gearbox may be coupled to the shaft at its input and adapted to provide an output at an increased torque and reduced rotational speed relative to a rotation of the shaft. The implantable device may also include a decoupling mechanism, which includes a clutch plate and a coil spring. The clutch plate may be biased by the coil spring such that the decoupling mechanism rotates with the output of the gearbox in a first position and rotates independently of the output of the gearbox in a second position. A spool may be coupled to the output of the gearbox. The implantable device may also include a tongue anchor adapted to engage with the base of the tongue. The implantable device may also include a tether having a first end coupled to the spool and a second end coupled to the tongue anchor, and arranged so as to be laterally displaced in response to an operation of the actuator mechanism. The decoupling mechanism may transition from the first position to the second position when a force on the coil spring exceeds a threshold value and returns to the first position when the force on the coil spring is below the threshold value.

BRIEF DESCRIPTION OF THE DRAWINGS

The features, objects, and advantages of embodiments of the disclosure will become more apparent from the detailed description set forth below when taken in conjunction with the drawings, in which like elements bear like reference numerals.

DETAILED DESCRIPTION OF THE INVENTION

Figure 1A:
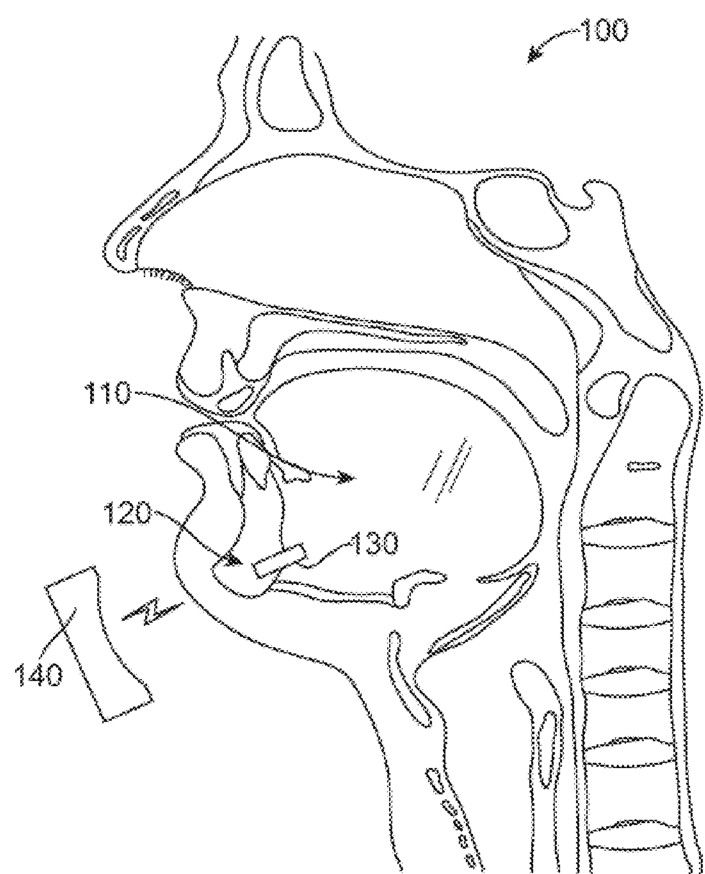
FIG. 1A shows cross-section of a tongue implant system implanted within a patient, according to an embodiment of the invention.

Techniques for operating a subcutaneous implant device are disclosed. The implant device can be formed of a non-magnetic material that is compatible with diagnostics such as magnetic resonance imaging (MRI) and can include a rotor element that rotates under the influence of an external magnetic field. The implant device can provide a tension relief mechanism to prevent excessive loads from damaging the device and harming the patient. A non-implanted device can include a stator and drive circuitry for generating the external magnetic field. The non-implanted device can receive a user command and can vary the external magnetic field based on the command. When activated by the magnetic field, the implant device changes its operating state and thereby interacts with the patient's body. Applicants' co-pending application Ser. No. 12/250,398, filed on Oct. 13, 2008, discloses additional details relating to embodiments of the present invention and is expressly incorporated herein by reference for all purposes FIG. 1A is a simplified diagram of a tongue implant system 100, according to an embodiment of the present invention. In the diagram, element 110 refers to the tongue and element 120 is the mandible. The implant system 100 includes an implant 130 that is inserted into a patient's body and a non-implanted portion 140 that is external to the patient. The non-implanted portion 140 can control operation of the implant 130 to avoid obstruction of the airway passage by interacting with tongue 110.

In some embodiments, implant 130 includes an anchor portion, an actuator, and a connecting member. The anchor portion is used to secure implant 130 to the mandible 120 and can include a titanium bracket and titanium bone screws. The actuator can be a transducer which converts a rotating external magnetic field into a rotational motion. For example, the actuator can include a conductor configured to rotate under the influence of the external magnetic field. The connecting member is disposed between the actuator and the tongue so that, depending upon its direction, rotation of the actuator can interact with the tongue.

The connecting member can include mechanical means such as a shaft or screw arrangement which translates the rotation of the actuator into a linear motion. In some embodiments, the connecting member includes a flexible portion or a fiber that is securely attached to the base of the tongue at one end and to the shaft or screw at the other end. Rotation of the actuator is thus translated into a linear displacement of the connecting member which interacts with the tongue to produce the desired action. The connecting member can also include a tension relief mechanism, such as a spring assisted clutch, which disengages all or a portion of the connecting member when a pulling force acted on the connecting member exceeds a predetermined threshold.

Non-implanted portion 140 is configured to control operation of the implant 130. In some embodiments, non-implanted portion 140 (also "controller") includes a housing that is adapted to interface with a patient's body at or near where the implant 130 is located. As shown, the controller 140 has a contoured portion which receives the patient's chin. The contoured portion enables the controller to partially surround the implant 130 so that it faces the implant on several sides. For example, when engaged with the patient, controller 140 can form a roughly hemispherical coverage area with respect to the implant.

Controller 140 can be configured to produce magnetic fields for operating the implant. In one embodiment, controller 140 includes a stator element. The stator can have a ferromagnetic core. The ferromagnetic core can be formed from a single piece of material. In some embodiments, the ferromagnetic core is formed from a plurality of laminations. The stator element can have multiple poles each of which is adapted to receive a conductive winding. The number of poles and windings can vary. In some embodiments, the stator element has four poles and two conductive windings arranged so that each winding spans two different poles.

Figure 1B:
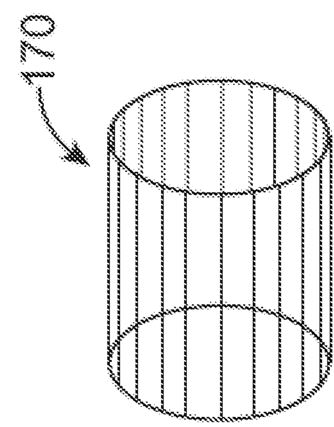
FIG. 1B is a schematic diagram illustrating power transfer aspects of a tongue implant system, according to an embodiment of the invention.
Figure 1B:
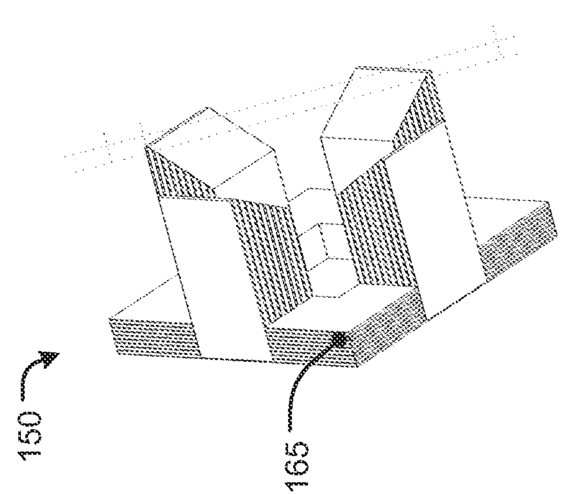

FIG. 1B is a conceptual diagram illustrating aspects of implant system 100. This diagram shows interaction between a stator element 150 and a rotor element 170. The stator 150 is part of controller 140 and is shown in a position external to the patient's body near the site of the implant. The rotor 170 is part of the actuator portion of implant 130 and is located beneath the skin. Other aspects of the implant 130 and non-implanted portion 140 are omitted for clarity in describing the interaction between stator 150 and rotor 170.

Stator 150 includes windings (not shown) and core 165 Core 165 has four elongated poles with chamfered ends with each pole providing support for an associated winding. In operation, a driver circuit supplies an alternating current to the windings and controls a phase relationship between the current flows. The alternating current in each winding creates a changing or magnetic field which can pass through the patient's body in the vicinity of the rotor 170. When taken together, the alternating currents produce a magnetic field that shifts or rotates in relating to the stator 150. The direction of the rotating field and the field strength can be changed by controlling current flows.

Rotor 170 moves under the influence of the changing magnetic field. As shown, rotor 170 can be a hollow, cylindrical structure capable of spinning about an axis within the implant device. The rotor 170 can have a solid surface (e.g., a tube) or a surface with one or more openings. In one embodiment, rotor 170 can have a squirrel-cage design having a plurality of elongated conducting members joined at each end by a ring. Many variations of rotor 170 are possible within the scope of the present invention.

Preferably, rotor 170 is formed of a non-magnetic material such as copper. Other suitable, non-magnetic materials can include gold and silver. In some embodiments, implant 130 is constructed entirely of non-magnetic materials to avoid interface with magnetic resonance imaging (MRI) and other diagnostics. The magnetic field from stator 150 can induce a current flow in rotor 170. Interaction between the induced current and the rotating magnetic field causes rotor 170 to spin or turn about its axis. Implant 130 can thus convert energy from the external magnetic field into mechanical energy that is used to interact with the tongue.

Controller 140 can include a user-interface for controlling operation of the implant system 100. For example, prior to sleeping, the patient may choose to restrict movement of the tongue in order to avoid closure of the airway passage. Upon waking, or when treatment is no longer desired, the user can activate implant 130 and release the tongue for unrestricted movement. In one embodiment, controller 140 supports at least SET and RELEASE commands for changing the state of implant 130 in connection with its operation. In some embodiments, status indicators are also provided and can indicate, for example, when the controller 140 is properly positioned for operating the implant 130.

Figure 1C:
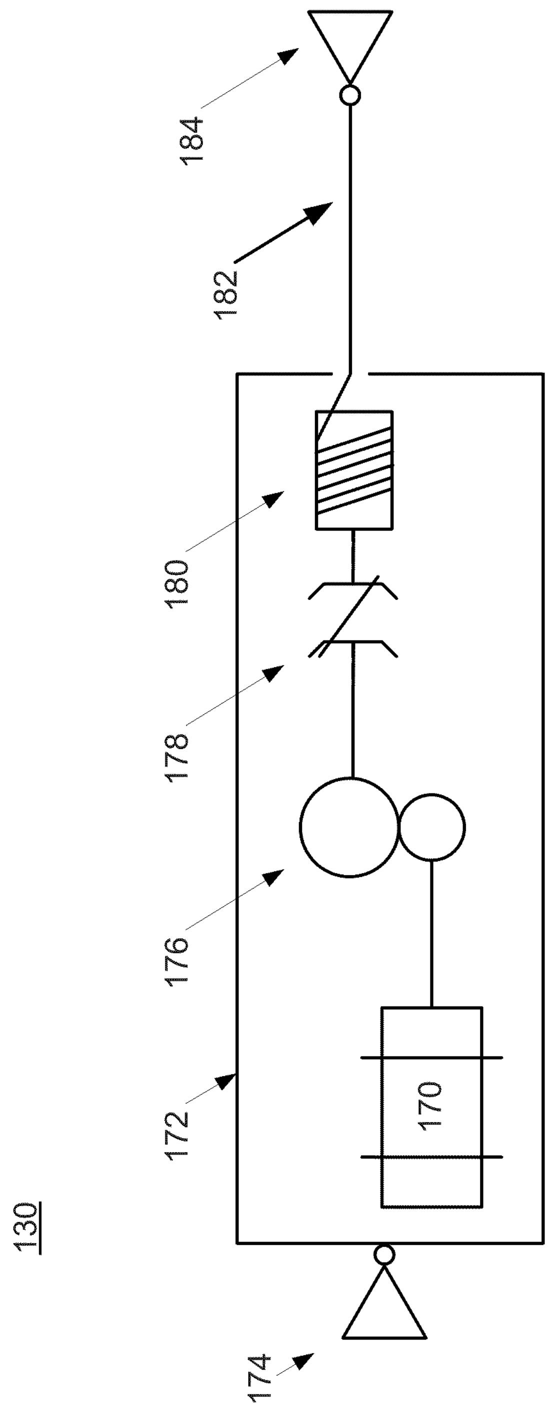
FIG. 1C is a schematic diagram of a tongue implant device, according to an embodiment of the invention.

FIG. 1C is a simplified schematic diagram of the implant 130, according to an embodiment of the invention. The implant includes a housing 172, which is generally constructed from an MRI safe and biocompatible material such as titanium, stainless steel or a polymer material. The housing 172 may be configured to attach to a mandible via mandibular anchor 174, which can be hingeably attached to the housing 172. The rotor 170 is located within the housing 172, and securely attached within. The output of the rotor 170 is operatively coupled to a torque multiplying mechanism 176. The torque multiplying mechanism 176 is configured in increase the output torque of the rotor, and may comprise a gearbox, or more specifically a planetary gearbox, spur gear train, work gear, hydraulic pump, pneumatic pump, friction clutch, screw mechanism, spring mechanism, compressed ball bearing mechanism, and pulley system.

The output of the torque multiplying mechanism 176 is operatively coupled to a tension relief mechanism 178, which in turn is operatively coupled to a spool 180, which is in turn operatively coupled to a linking mechanism 182. The linking mechanism 182 may be configured as one or more flexible tethers, each including one or more rigid structures, such as tongue anchors 184, for secure attachment to the base of the tongue. The linking mechanism 182 is configured to wrap around spool 180, which upon rotation will increase or decrease the length of the linking mechanism 182 which extends out of the housing 172.

The tension relief mechanism 178 is configured to disengage the spool 180 from the torque multiplying mechanism 176 when a pulling force applied to the linking mechanism 182 exceeds a predetermined threshold force value. In some embodiments, the pulling force is less than 10 N and the threshold force value is greater than 1 N. In other embodiments, the pulling force is in the range of 2-5 N and the threshold force value is greater than 2 N. The threshold force value is generally selected to prevent the linking mechanism 182 and/or tongue anchor 184 from breaking, dislodging from the tongue, and/or permanently deforming. After the tension relief mechanism 178 has been disengaged and the threshold puling force has subsided, the tension relief mechanism 178 may reengage the spool 180 to the torque multiplying mechanism 176 for later actuation of the tongue.

The pulling force is applied to the linking mechanism 182, and thus to the outer diameter of the spool 180. This will cause a torque to be applied to the tension relief mechanism 178 via the spool 180. In some embodiments, the tension relief mechanism 178 may be a clutch configured to slip or completely disengage when a threshold torque corresponding to the threshold force value is applied thereto. The tension relief mechanism 178 may include a mechanism, such as a tensioned coiled spring, which begins to elongate to help disengage the tension relief mechanism 178 when the threshold force value is applied.

Figure 1D:
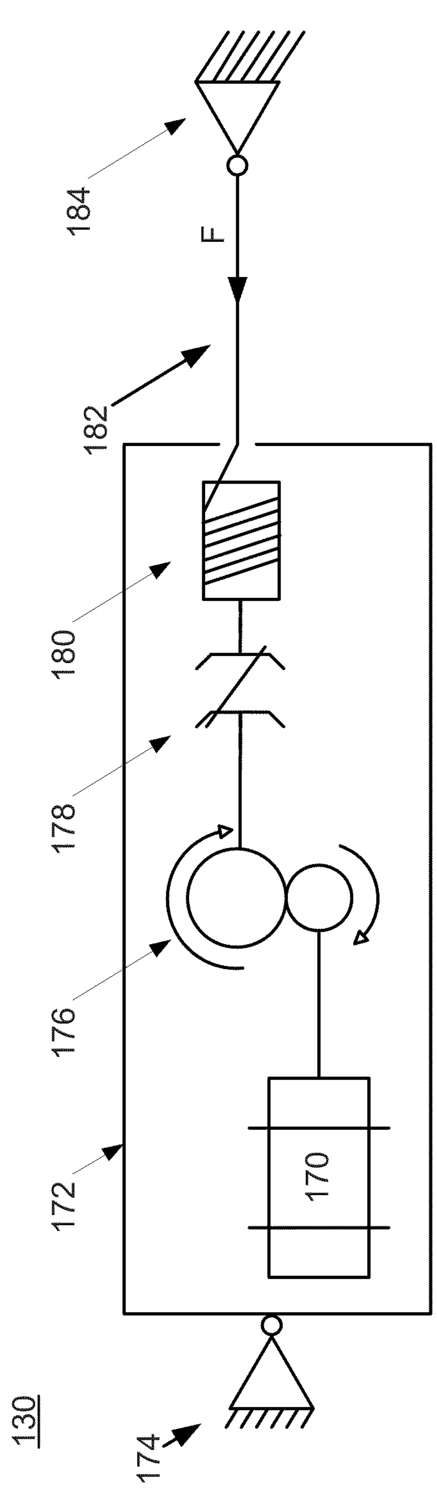
FIGS. 1D and 1E are schematic diagrams of the tongue implant device of FIG. 1C in use, according to various embodiments of the invention.
Figure 1E:
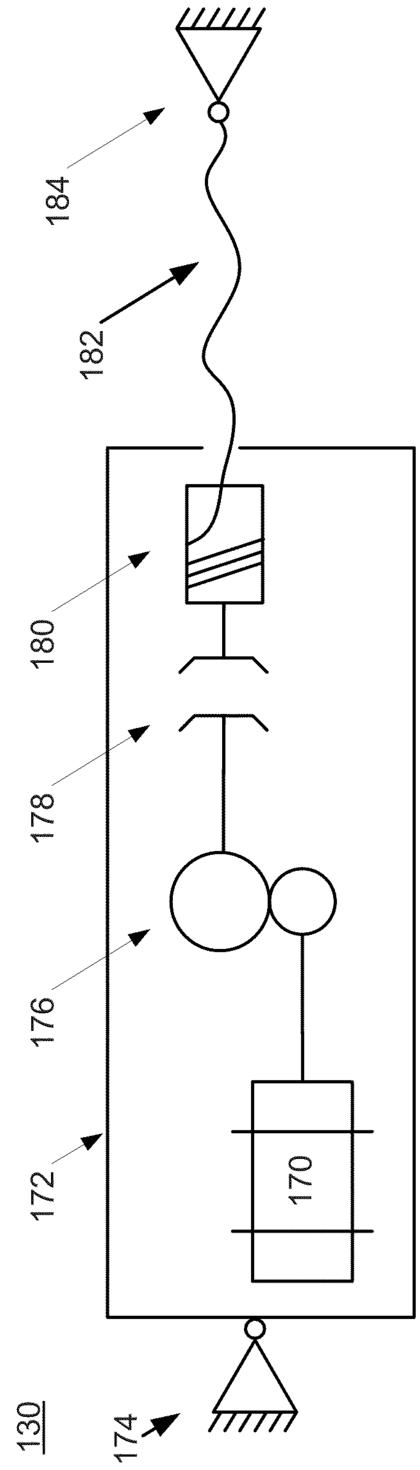

FIGS. 1D and 1E show simplified schematic diagrams of the implant 130 in use, according to an embodiment of the invention. The implant 130 has been implanted within a patient, with the mandibular anchor 174 surgically attached to the mandible and the tongue anchor 184 surgically attached to the base of the tongue.

With reference to FIG. 1D, the patient or another operator can cause the rotor 170 to actuate via use of the controller 140 as described herein. The rotor 170 will accordingly actuate the torque multiplying mechanism 176 to rotate the spool 180 via the engaged tension relief mechanism 178. The spool 180 rotates and thereby applies a pulling force F to the linking mechanism 182 by winding the linking mechanism there about, and thus draws the tongue anchor 184 towards the mandibular anchor 174. The rotor 170 will stop rotating after the tongue anchor 184 has moved a predetermined distance or when the controller 140 is controlled by the patient to stop generating the magnetic field that drives the rotor 170. The linking mechanism 182 maintains a stabilizing force onto the tongue anchor 184 to hold the tongue in position so as not to block the airway. The rotor 170 may be reversed from the state shown in FIG. 1D to a relaxed state by use of the controller 140. Accordingly, the rotor 170 will rotate in an opposite direction to unwind the spool 180 and slacken the linking mechanism 182. This causes the tongue anchor 184 and the connected tongue to move back into a non-tensioned position. In a slackened state, the linking mechanism 182 may apply a slight tension to the tongue anchor 184 to prevent excessive slack. The slight tension is generally small enough to go unnoticed by the patient.

With reference to FIG. 1E, the tension relief mechanism 178 will disengage when a threshold amount of pulling force is externally applied to the linking mechanism 182. The threshold amount of force is generally the sum of the stabilization force maintained by the linking mechanism as shown in FIG. 1D and the external pulling force, and is below a force which will cause dislodgment of the tongue anchor 184. This generally will occur when the muscles of the tongue pull against the linking mechanism 182, which can be an involuntary action by the patient when asleep. The tension relief mechanism 178 can include a clutch, which slips or completely disengages the spool 180 when a compressed element (e.g., spring) of the clutch is overcome due to the threshold pulling force being applied. Accordingly, the linking mechanism 182 will slacken and allow the tongue anchor 184 and the attached portion of the tongue to be placed back into non-tensioned position. Disengagement of the tension relieve mechanism 178 prevents damage from occurring to portions of the implant 130, and or the patient from forcible removal of the anchors from the patient. The tension relief mechanism 180 may be reengaged after the pulling force has reduced below the threshold, and thus allow the linking mechanism 182 to be tensioned again and placed back into the position shown in FIG. 1D.

Figure 2A:
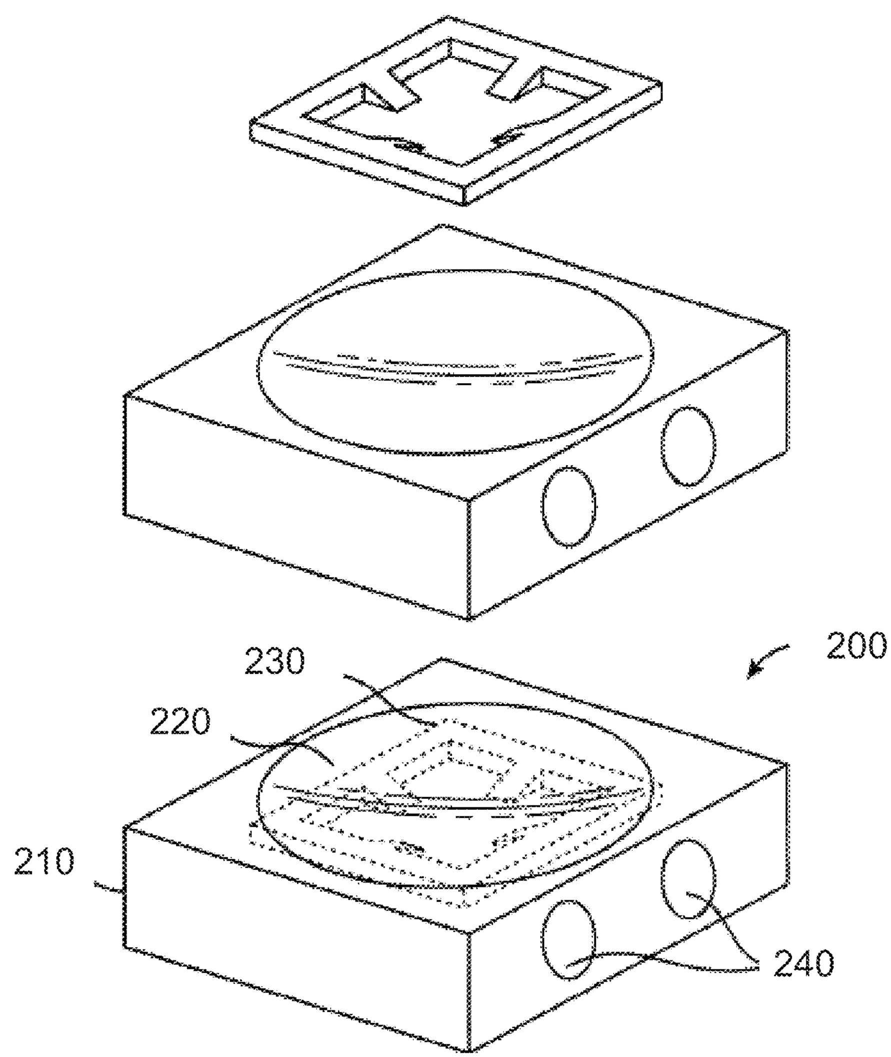
FIG. 2A shows exploded and complete perspective views of a device for controlling a tongue implant, according to an embodiment of the invention.

FIG. 2A is a diagram of a non-implanted device 200 (also known as a controller) for operating a tongue implant according to embodiments of the present invention. The non-implanted device 200 includes a housing 210 having a contoured area 220 for interfacing with a patient's body. As illustrated, a stator element 230 is disposed within the housing near the contoured area. In some embodiments, the stator 230 has a plurality of poles each with a chamfered end feature. For example, the chamfered end features can have a reduced cross-sectional area that tapers to the interior portion of the stator 230. The taper of the stator-poles can create a recessed area for receiving the patient's chin. When engaged with the patient, the poles are exposed to different parts of the implant which can facilitate effective coupling of the stator's magnetic field and the conducting members of an implanted rotor.

Non-implanted device 200 can also include user interface elements. For example, buttons 240 can be included for controlling operation of the implant. Status indicators such as light-emitting diodes can also be included. In one embodiment, buttons 240 correspond to a SET and RELEASE command for changing the state of the implant. One or more status indicators can be included to aid in aligning the non-implanted device 200 with the implant and for signaling a low-battery condition, etc.

Figure 2B:
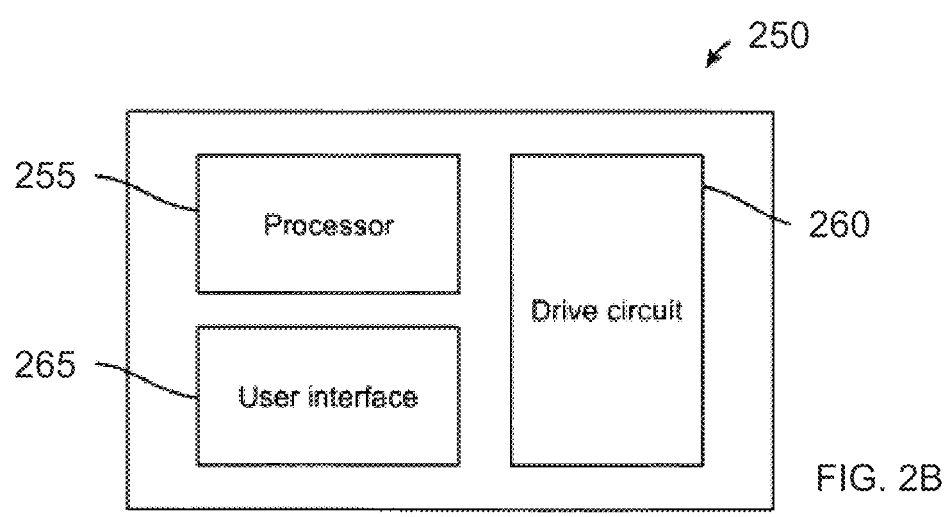
FIG. 2B is a functional block diagram of an implant control circuit, according to an embodiment of the invention.

FIG. 2B is a functional block diagram of a tongue implant control circuit 250 such as can be used with non-implanted device 200. As shown, control circuit 250 includes a processor 255, a drive circuit 260, and a user interface 265. Processor 610 can be a microprocessor, microcontroller, field programmable gate array (FPGA), application specification integrated circuit (ASIC), or the similar device. Processor 255 is configured to receive input/output signals from the user interface 265 and to control the operation of the drive circuit 260.

Drive circuit 260 can be coupled to the stator element (e.g., stator 150, etc.) for controlling current flows in its windings. For example, drive circuit 265 can be a two-phase driver which delivers current to a 0° phase winding and a 90° phase winding for generating a rotating magnetic field. The present embodiment is not limited to a two-phase driver, but may include any number of windings and alternating currents arranged so as to create a magnetic field having a desired intensity and other properties.

In use, processor 255 receives a command for controlling the implant from user interface 265. For example, the command can be a SET command for restricting movement of the tongue, a RELEASE command for restoring full tongue movement or some other command. Based on this command, processor 255 causes drive circuit 260 to energize the stator windings and to thereby create a rotating magnetic field. The direction in which the field rotates corresponds to the command received. For example, the drive circuit 260 can set up current flows to create a clockwise magnetic field or a counter-clockwise magnetic field as directed by processor 255.

Processor 255 can also perform safety and positioning functions. In some embodiments, processor 255 monitors the level of current flowing in the stator windings and causes drive circuit 255 to reduce the current or to deenergize the stator if the current exceeds a predetermined level. Also, processor 255 can detect the presence of the implant based on stator currents. For example, processor 255 can detect a drop in current flow associated with magnetic coupling to the implant. In some embodiments, processor 255 signals the proximity of the implant by generating audible tones or flashing LEDs at the user interface 265. By varying duration of the tones or a flash-rate, a user can guide in proper positioning and alignment of the non-implanted device.

Figure 3:
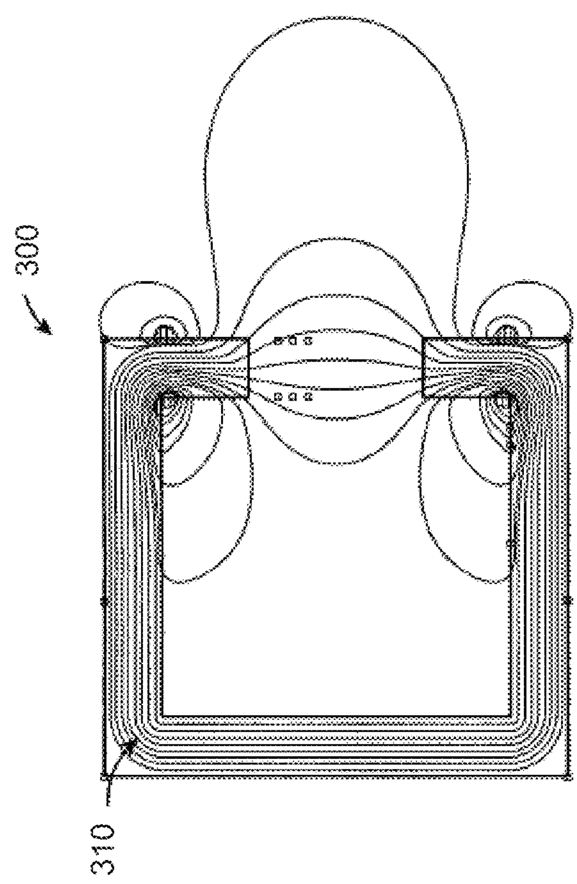
FIG. 3 is a magnetic flux diagram showing aspects of an external magnetic field, according to an embodiment of the invention.

FIG. 3 is a conceptual diagram showing aspects of the magnetic field 300 created by a non-implanted device according to embodiments of the present invention. In the diagram, core element 310 approximates the stator of the non-implanted device. When current flows in the stator windings north and south magnetic poles are created in the stator core. The magnetic poles, in turn, are linked by flux lines which can span the air gap between physical poles of the stator core.

Portions of the magnetic flux extend out from the stator core and magnetically couple with the conductors of the implanted rotor. When the magnetic fields linking opposing poles of the stator rotate, a torque is exerted on the rotor. Assuming a winding fill ratio of approximately 63%, analysis has shown that a four-pole stator according to embodiments of the present invention can generate a magnetic field of sufficient intensity for operating an in-vivo tongue implant device. In some embodiments, a field intensity greater than 0.2 T can be generated by the stator at a distance of approximately 10 mm. Analysis indicates that this field intensity can generate a torque of at least 1.5 μN·M and is believed to be sufficient for displacing the tongue.

FIGS. 4A-4F illustrate different stator designs for use with embodiments of the present invention. The various stators can be formed of a ferromagnetic material. In some embodiments, the stators include a plurality of laminations which can, for example, reduce the effect of eddy currents in the core structure.

Figure 4A:
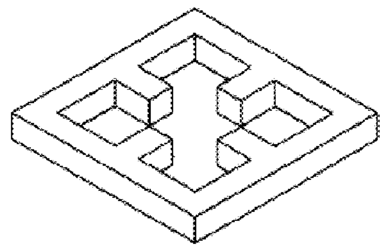
FIGS. 4A-4F show various views of stators, according to various embodiments of the invention.

FIG. 4A is a four pole stator in a substantially flat rectangular configuration. The stator can be sized to approximately 80 mm on each side and can have a thickness of approximately 10 mm. As illustrated, each pole is uniformly spaced and extends approximately 15 mm into the interior area. In a preferred embodiment, each pole includes a chamfered end feature for receiving a patient's chin. For example, the chamfered poles can slope inward to form a bowl for placement of the chin.

Figure 4B:
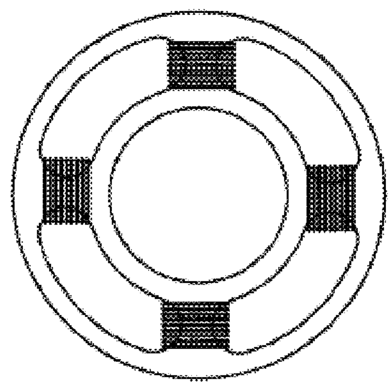
Figure 4C:
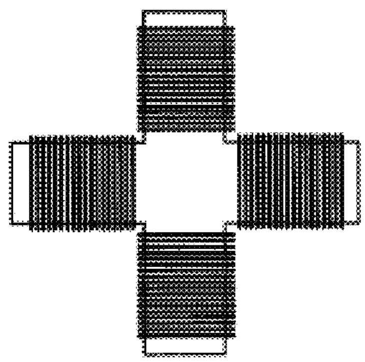
Figure 4D:
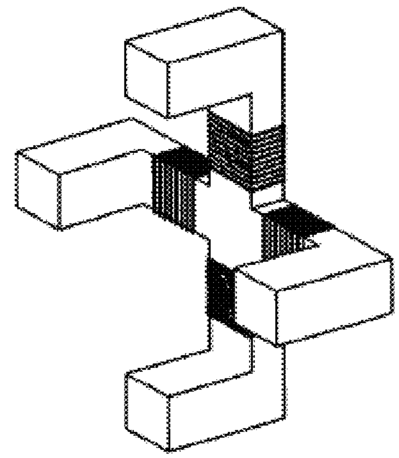
Figure 4E:
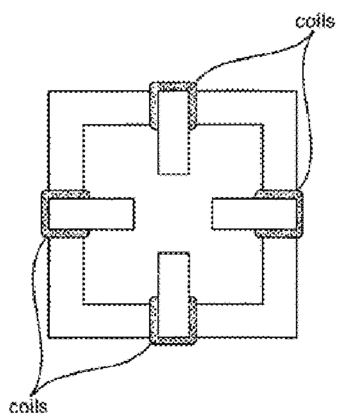
Figure 4F:
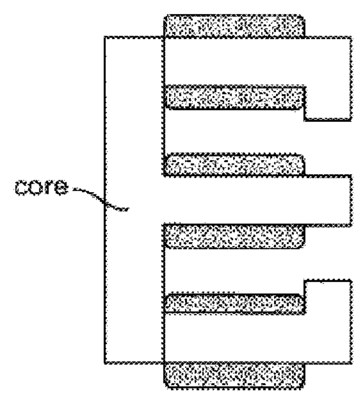

FIG. 4B is an end-view of a cylindrical stator. As shown, windings about the poles extend the length of the stator and each is pole is joined to a central circular support element. FIG. 4C is a cross-shaped stator which can be substantially flat. Windings cover opposing legs of the cross. FIG. 4D is a modified cross-shape with legs that extend out from the central axis. As with the chamfered end features, the legs can be arranged so as to accommodate placement with the chin. FIGS. 4E-4F are top views of alternative stator designs. These stators are designed to facilitate patient-positioning while maintaining a substantially flat external surface.

Figure 5:
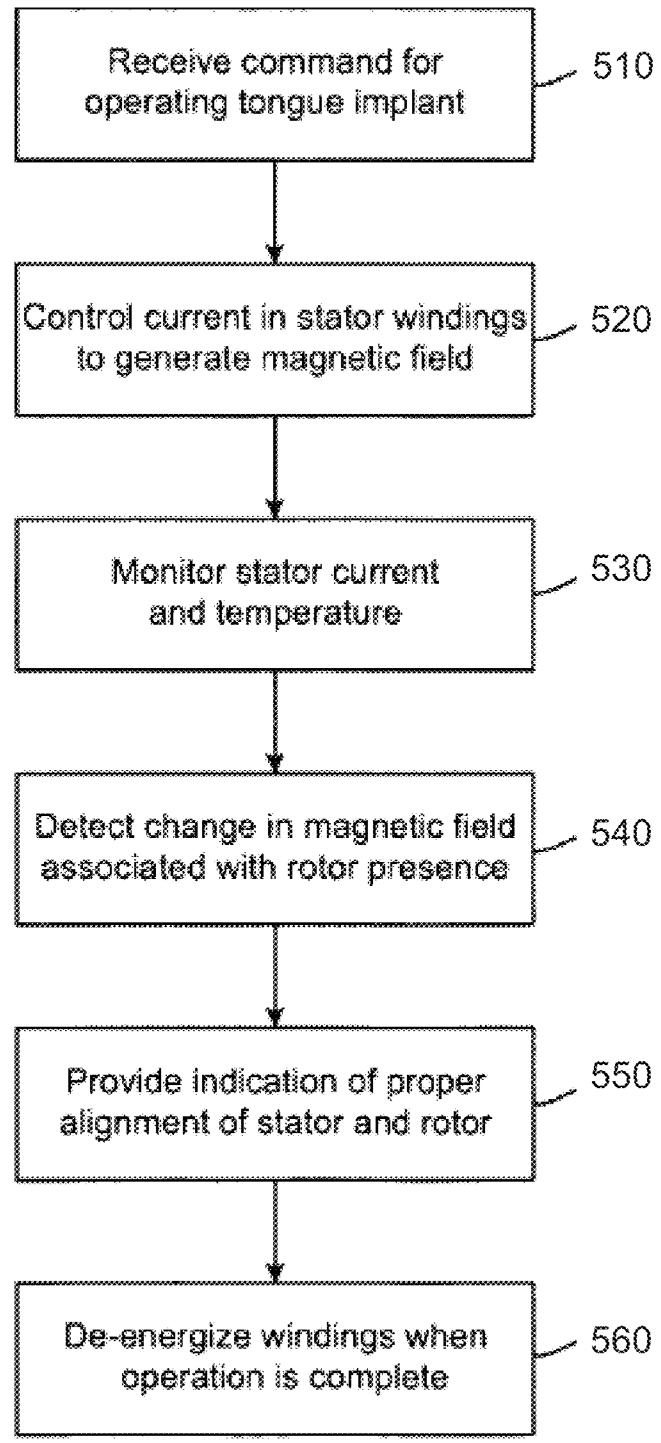
FIG. 5 is an exemplary flowchart of a method for operating a tongue implant, according to an embodiment of the invention.

FIG. 5 is a flowchart illustrating steps for operating a tongue implant. These steps can be executed by processor (e.g., processor 255) or other control circuitry used with a non-implanted device such as described herein. At block 510, a command for operating the implant is received. The command can be a user command for restricting the tongue, releasing the tongue, or it can be some other command relating to the implant.

At block 520 the non-implanted portion determines a current flow in the stator windings in response to the user command. The stator is external to the patient and current flow in the stator windings is controlled so as to produce a rotating magnetic field. The direction of rotation can be determined according to the user command. For example, clockwise rotation may be used to restrict the tongue and counter-clockwise rotation may be used to release the tongue depending upon the mechanical arrangement of the implanted rotor.

In some embodiments, the amount of current delivered to the stator windings is determined so as to create a magnetic field having a predetermined intensity when measured at a distance separating the non-implanted portion from the implant device. For example, the current flow may be determined so that the intensity of the magnetic field is at least 0.16 T at a typical separation distance of 10 mm.

At block 530 the stator current and temperature are monitored. If, at any time, unsafe levels of current or temperature are detected, the stator windings can be immediately de-energized or the current level can be reduced and a user of the device can be notified of the condition.

When the non-implanted device is engaged with the patient, the magnetic field couples with the implanted rotor and stator current changes. This change can vary with rotational speed and the alignment of stator and rotor elements. For example, when the non-implanted portion is first activated, stator current increases. As the rotor spins up and rotational speed stabilizes, stator current may decrease to a steady operating level.

At block 540 the non-implanted portion detects the level of stator current flow, and at block 550 an alignment indicator is provided. For example, the non-implanted portion can measure the increase in stator current and/or the steady operating level, and compare it with a threshold value (or collection of values) representative of a proper alignment between the stator rotor elements. Based on the comparison, the alignment indicator can signal an insufficient coupling and alert the user to adjust the position of the non-implanted portion accordingly. When the implant operation is completed, at block 560, the stator windings are de-energized and the process completes.

FIGS. 6A-6E show an implant 600 in various views, according to an embodiment of the invention. Implant 600 shares a similar mechanical configuration as described with reference to implant 130.

Figure 6A:
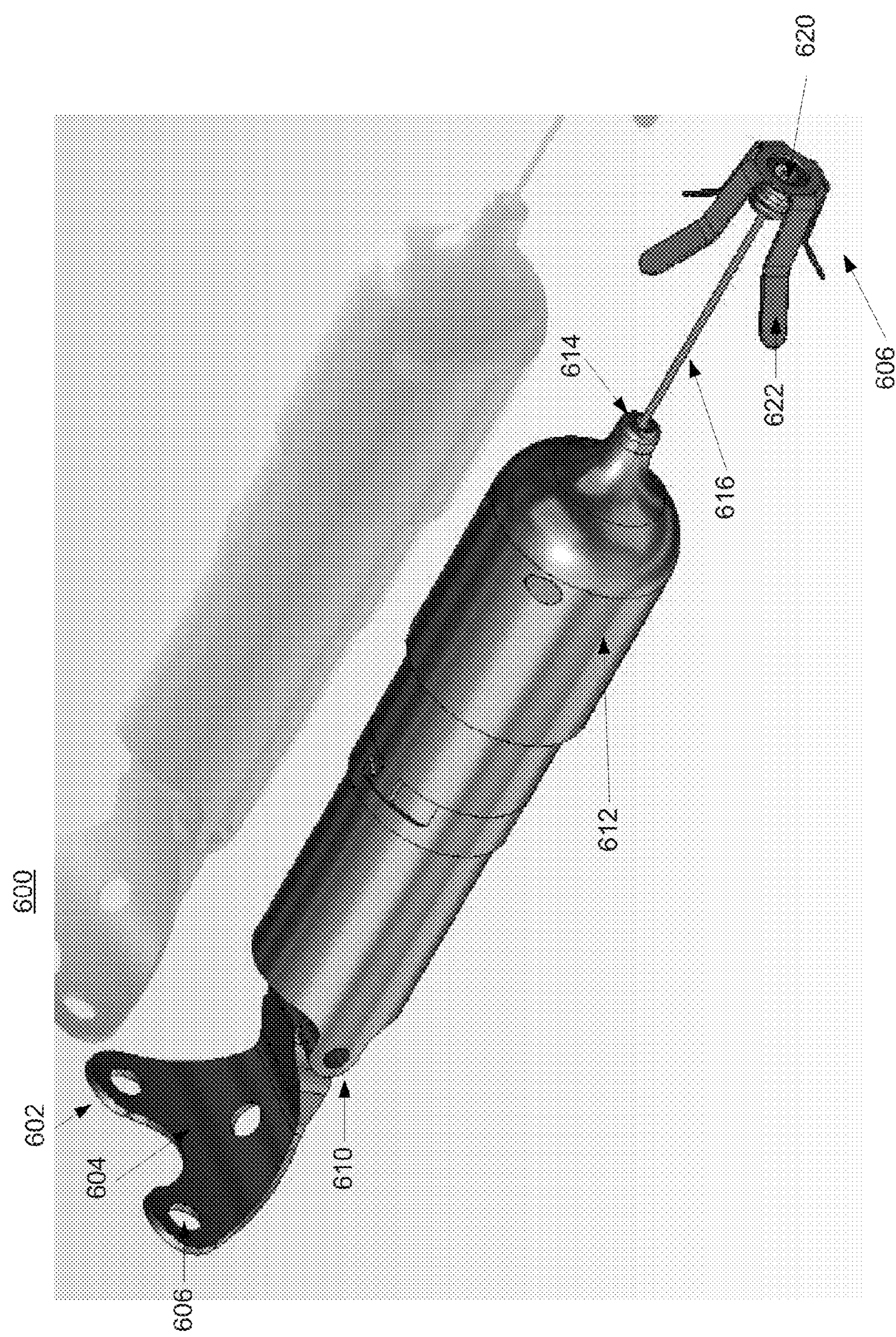
FIG. 6A is a perspective view of a tongue implant device, according to an embodiment of the invention.

With reference to FIG. 6A, implant 600 includes a mandibular anchor 602, that is configured for surgical attachment to a jaw of a patient. The mandibular anchor 602 includes a curved inner surface 604, that is curved to match to wrap around the mental protuberance (i.e., chin) of the mandible of the patient. The mandibular anchor 602 includes holes 606 which allow screws to pass through and attach to the mandible. The mandibular anchor 602 may be constructed from various biocompatible metals (e.g., stainless steel, titanium) and/or polymers. The mandibular anchor 602 may be malleable to allow a surgeon to form the inner surface 604 to the chin profile of a particular patient.

Mandibular anchor 602 is hingeably attached to a housing 608. The housing 608 is configured as a cylinder having a hinge 610 that couples to the mandibular anchor 602. The housing 608 may be constructed from an MRI safe and biocompatible metal (e.g., stainless steel or titanium) or polymer. An end cap 612 is connected to the housing 608, and is constructed in a similar fashion. The end cap 612 includes an opening 614 which a linking section 616 exits from.

The linking section 616 may be constructed from a flexible chord, such as a reinforced polymer (e.g., braided Kevlar) or braided stainless steel which is capable of withstanding a high tension load, and which is capable of withstanding many load cycles. The linking section 616 is attached to a tongue anchor 618. The tongue anchor 618 is configured for long-term implantation within the base of a patient's tongue. The tongue anchor 618 includes a central member 620 from which a plurality for anchor arms 622 extend from. Four anchor arms 622 are shown; however, in some embodiments more or less anchor arms 622 may be used. The anchor arms 622 may be constructed from a relatively stiff and resilient MRI safe and biocompatible material, such as stainless steel or titanium, which is capable of withstanding a high tension load, and which is capable of withstanding many load cycles.

Figure 6B:
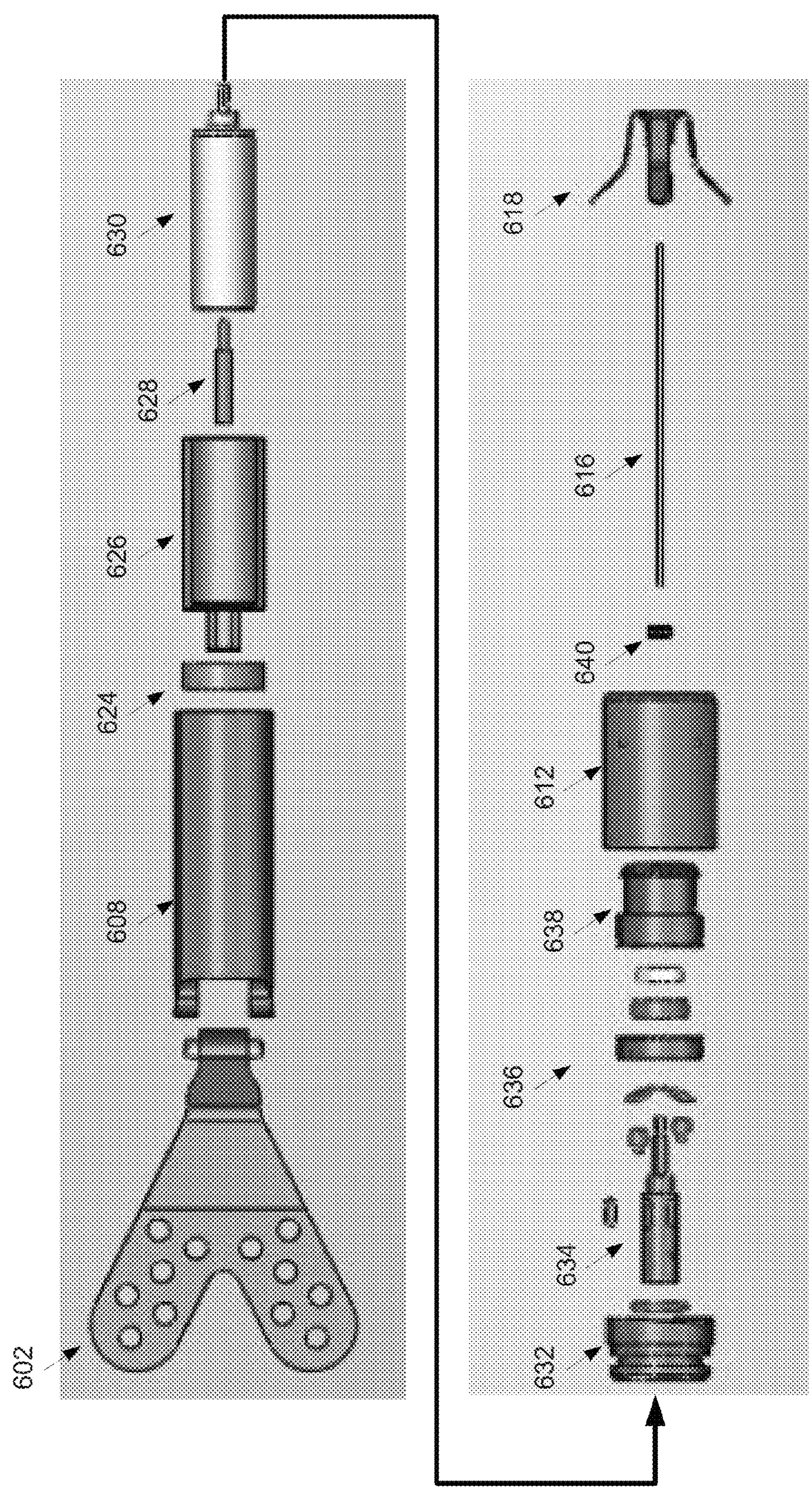
FIG. 6B is an exploded side view of the tongue implant device of FIG. 6A.

Interior portions of the implant 600 are shown in the exploded view of FIG. 6B. Housing 608 holds a bearing 624, which supports a rotatable rotor 626. The bearing 624, and all bearings of the implant 600, can utilize ceramic ball bearings to avoid corrosion. The rotor 626 can be a squirrel-cage rotor in which a plurality of elongated conducting members is joined at each end by a ring. A rotor output shaft 628 is connected to the rotor and can rotate therewith. The rotor output shaft 628 is coupled to a gearbox 630. In this embodiment the gearbox 630 is configured as a planetary gearbox with a cylindrical housing, which resides within the rotor 626. Alternatively, the gearbox 630 can comprise a spur gear train, work gear, hydraulic pump, pneumatic pump, friction clutch, screw mechanism, spring mechanism, compressed ball bearing mechanism, or pulley system. The gearbox 630 can include a locking or anti-back drive feature, such as a moveable pin or pawl actuated by an external electric field, which prevents movement of the gearbox 630 when not powered.

In some embodiments the gearbox 630 can have a 256:1 input/output ratio, i.e., for every 256 revolutions of the rotor output shaft 628, the gearbox will output one revolution. Conversely, torque will be increased at the output of the gearbox 630 at an input/output ratio of 1:256, i.e., for every unit of torque the rotor output shaft 628 transmits to the gearbox 630, the gearbox will output 256 units of torque. Many other gearbox ratios can be used according to the power output of the rotor 626.

Housing cap 632 is attached to the end of the housing 608 and rotatably supports an output shaft 634 of the gearbox 630 via a bearing. A tension relief mechanism 636 is coupled to the output shaft 634. A portion of the tension relief mechanism 636 rotates with the output shaft 634. The tension relief mechanism 636 is further configured to moveably engage and disengage with a rotatable spool 638. The linking section 616 can be wrapped around the spool 638. Accordingly, rotation of the spool 638 causes the linking section 616 to extend out of or retract within the end cap 612, depending on the direction of rotation. The linking section 616 slides within a wiping seal 640 of the end cap 612, to help prevent tissue and liquids from entering.

Figure 6C:
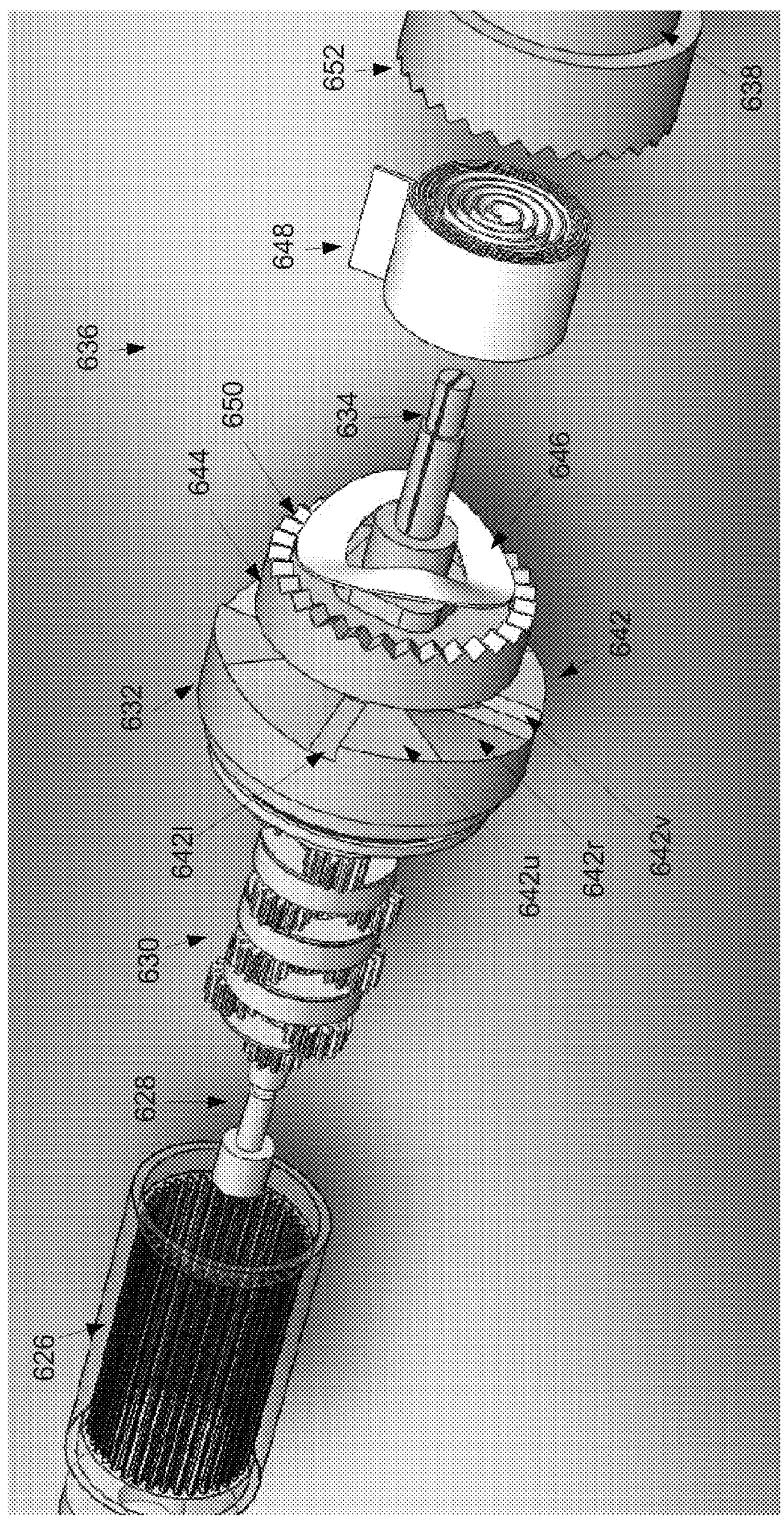
FIG. 6C is an exploded partial perspective view of the tongue implant device of FIG. 6A.

A detailed portion of tension relief mechanism 636 is shown in FIG. 6C. The housing cap 632 includes a cam surface 642 which includes multiple ramps 642*r*, vertical surfaces 642*v*, and horizontal surfaces 642*u*/642*l* of different heights. A rotatable clutch plate 644 engages the housing cap 632. The clutch plate 644 is longitudinally moveable and rotatable along and about the output shaft 634, with respect to the stationary housing cap 632.

Clutch plate 644 includes a plurality of followers (not shown in this view) configured as balls which engage the cam surface 642. A spring 646 applies a continuous longitudinal load onto the clutch plate 644 and the spool 638. Thus, as the spool 618 is rotatable, but longitudinally stationary, the spring 646 forces the followers (not shown) of the clutch plate 644 to continuously engage the cam surface 642. Accordingly, rotation of the output shaft 634 causes the clutch plate 644 to rotate and longitudinally move back and forth along the output shaft 634 and the cam surface 642. The vertical features 642*v* of the cam surface 642 can prevent the followers from freely rotating completely in the non-driven direction during a non-driven state, and thus act as a brake to the clutch plate 644 and output shaft 634. However, the rotor 626 may be driven in the non-driven direction (i.e., reverse) which will cause the followers to drive over the vertical features 642*v*.

Spring 646 is shown as a wave spring, but may be any device which applies a continuous longitudinal force (e.g., coil spring, diaphragm plate, etc.) when compressed. The spring 646 may apply enough longitudinal force to the spool 618 to prevent the spool 618 from freely rotating (i.e., when not engaged by the clutch plate 644) until a threshold amount of torque applied to the spool 618 overcomes the frictional holding forces applied by the spring 646. The interior portion of the spool 618 and/or an exterior portion of the spring 646 may include a frictional surface to increase the friction coefficient therebetween, and thus increase the threshold amount of torque required to rotate the spool 618.

Torsion spring 648 resides within the spool 638 with a first end attached to the output shaft 634 a second end attached to a portion of the spool 638, thus, the torsion spring 648 may apply a force therebetween when wound. The torsion spring is configured to wind (i.e., shorten and compress) in the driving direction of the spool 638, and may provide the linking section 616 with taught slack. When the followers (not shown) of the clutch plate 644 are riding along a high point of the cam profile of the cam surface 642, teeth 650 of the clutch plate 644 engage matching teeth 652 of the spool 638, and thus drive the spool 638 with the clutch plate 644 with the output shaft 634. In this engaging position the output shaft 634 and spool 638 rotate in kind, and thus the torsion spring 648 is not wound.

Conversely, when the followers (not shown) of the clutch plate 644 are riding along a low point of the cam profile of the cam surface 642, teeth 650 of the clutch plate 644 disengage from the matching teeth 652 of the spool 638. It should be understood that other engaging surfaces besides teeth can be used, such as frictional surfaces. In the disengaged position, the output shaft 634 rotates with respect to the stationary spool 638, and thus the torsion spring 648 is wound. The torsion spring 648 is prevented from unwinding the spool 638 as the spool 638 is held in position from the longitudinal force applied by the spring 646. Accordingly, a complete driven rotation of the clutch plate 644, when driven by the output shaft 634, will have at least one engaged position where the spool 638 is driven to rotate, and at least one disengaged position where the torsion spring 648 is wound and the spool 638 is held stationary. Reversing the drive direction will accordingly unwind spool 638 and torsion spring 648 in a similar fashion.

The clutch plate 644 will disengage from the spool 638 when not being driven by the output shaft 634, as the longitudinal force applied by the spring 646 will cause the clutch plate 644 to rotate slightly in the non-driven direction until the followers are stopped by the vertical surfaces 642*v* of the cam surface 642 of the stationary housing cap 632. This prevents the clutch plate 644 and output shaft 634 from rotating freely. Accordingly, in a non-driven wound position (i.e., clutch plate 644 disengaged, output shaft 634 non-driven, spool 638 wound), the torsion spring 648 is wound between the locked clutch plate 644 and the spool 638, to store potential energy therebetween. The torsion spring 648 may not be completely wound and thus can provide slack to the linking section 616. In the non-driven wound position, when a reverse torque load (i.e., tongue force applied in the reverse direction of driving) is applied to the wound spool 638 by the linking section 616, the spool 638 will be still held in place by the longitudinal force of the spring 646.

When the reverse torque load exceeds a predetermined threshold, the longitudinal force applied by the spring 646 will be overcome and the spool 638 can then rotate with respect to the clutch plate 644 and output shaft 634. This also will cause the torsion spring 648 to begin to elongate and release stored potential energy in the non-driven direction between the locked clutch plate 644 and the spool 638. This causes the spool 638 to unwind until the reverse momentum of the spool 638 is slowed and halted by the longitudinal force of the spring 646. When the spool 638 is unwound, any wound portion of linking section 616 is simultaneously unwound and slackened. The spring 648 can be configured to allow relative movement between the clutch plate 644 and the spool 638 when the threshold reverse torque corresponds to a threshold pulling force applied by the linking section 616 to the spool 638. In some embodiments, the pulling force is less than 10 N and the threshold force value is greater than 1 N. In other embodiments, the pulling force is in the range of 2-5 N and the threshold force value is greater than 2 N.

Figure 6D:
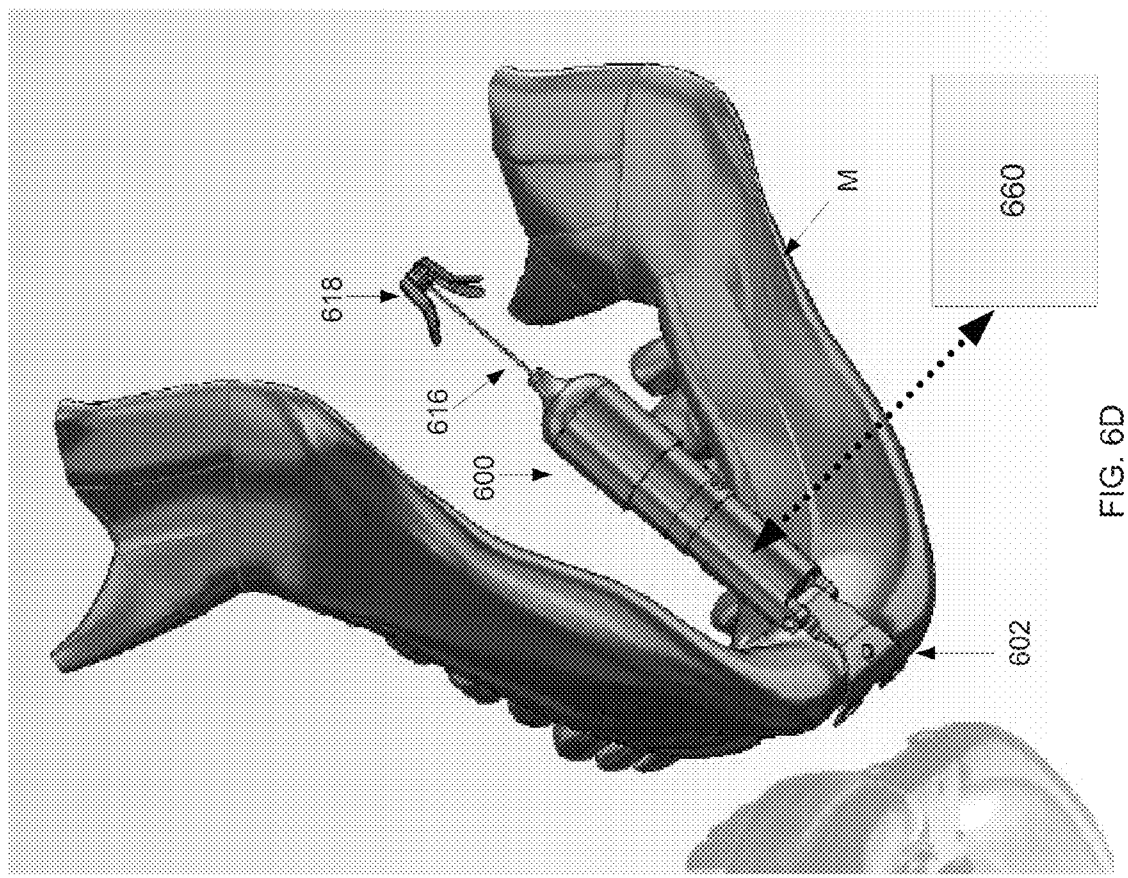
FIG. 6D is a perspective view of the tongue implant device of FIG. 6A in use, according to an embodiment of the invention.

FIG. 6D shows the implant 600 in use, according to an embodiment of the invention. The implant is shown implanted within a human patient. The mandibular anchor 602 has been surgically attached to the chin area of a mandible M and the tongue anchor 618 has been surgically attached to the base of the tongue (not shown). The patient may use an externally placed controller 660 (e.g., controller 140) to apply a magnetic field to the implant 600 and drive the rotor 626, typically before the patient goes to sleep. The linking section 616 will accordingly wind around spool 638 and withdraw into the end cap 612, while drawing the tongue anchor 618 closer to the chin. This causes increased space in the patient's airway to help prevent airway collapse and thus help apnea during sleep. When the patient awakens, the patient may use to controller 660 to reverse the rotor and unwind the linking section 616 from the spool 638, and thus slacken the linking section 616 and place the tongue and tongue anchor 618 into a non-tensioned position.

In some cases, the tongue may apply an involuntary pulling force onto the linking section 616. The pulling force may be high enough such that if not alleviated, the tongue anchor 618 would be forcibly dislodged from the tongue, resulting in injury. The tension relief mechanism 636 of the implant 600 can alleviate the excessive pulling force by decoupling the linking section 616. When the pulling force exceeds a predetermined threshold, a corresponding reverse torque threshold is applied to the spool 638. The pulling force threshold is less than the amount of force to dislodge the tongue anchor 618, but more than the pulling force required to keep the tongue in a tensioned position. The reverse torque threshold overcomes the holding force of the spring 646 and allows the wound torsion spring to lengthen and release energy to rapidly unwind the spool 638. As the spool 638 is unwound, the linking section 616 accordingly slackens and allows the tongue to assume a non-tensioned position and prevent forcible dislodgement of the tongue anchor 618. The spool 638 may be rewound at a later time to retighten the linking section 616. Accordingly, the implant 600 is capable of withstanding repeated cycles of the threshold pulling force without tongue anchor 618 failure, or requiring removal/surgical intervention of the implant 600.

FIGS. 7A-7D show various implant housings, according to various embodiments of the invention. The implant housings shown function mechanically in the same general manner as described with reference to implant 600.

Figure 7A:
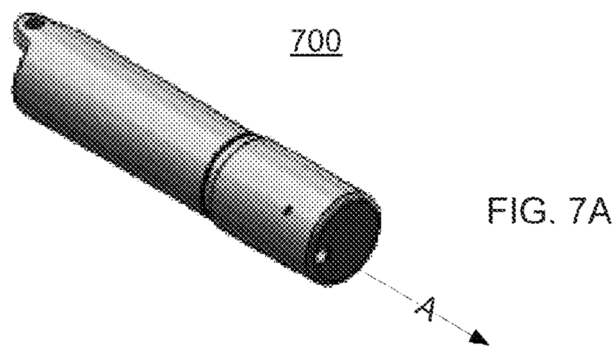
FIGS. 7A-7D are perspective views of tongue implant devices, according to various embodiments of the invention.
Figure 7B:
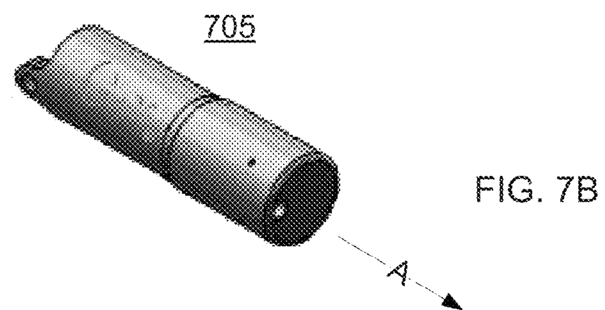

FIGS. 7A and 7B show implants housings 700 and 705. Implant housings 700 and 705 are cylindrical in shape. Implant housings 700 and 705 are configured to operate along pulling axis A, which extends between the mandible and tongue. Implant housing 700 has an approximate length of 41 mm and approximate diameter of 10 mm. Implant housing 705 has an approximate length of 32 mm and approximate diameter of 10 mm.

Figure 7C:
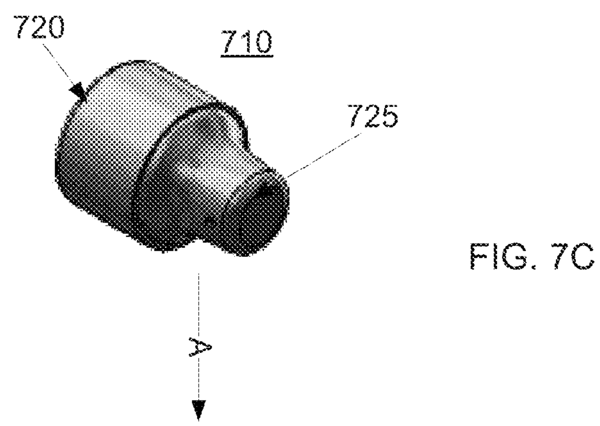
Figure 7D:
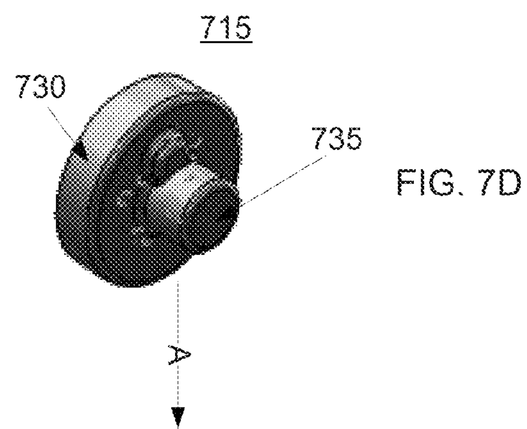

FIGS. 7C and 7D show implant housings 710 and 715. The implant housings 710 and 715 are configured to operate (i.e., spool) in an approximately transverse direction to the pulling axis A, which extends between the mandible and tongue. Implant housing 710 includes a cylindrical base 720 which truncates and tapers to an upper cylindrical portion 725. The cylindrical base 720 has an approximate diameter of 16 mm. The upper cylindrical portion 725 has an approximate diameter of 9 mm. The overall length of the implant housing 710 is approximately 21 mm.

With reference to FIG. 7D, implant housing 715 includes a cylindrical base 730 which adjoins an upper cylindrical portion 725. The cylindrical base 730 has an approximate diameter of 21 mm. The upper cylindrical portion 725 has an approximate diameter of 8 mm. The length of the cylindrical base 730 is approximately 5 mm, and the overall length of the implant housing 710 is approximately 11 mm. Utilizing the transverse layout shown in FIGS. 7C and 7D may, in some cases, provide a more compact implant.

Figure 7E:
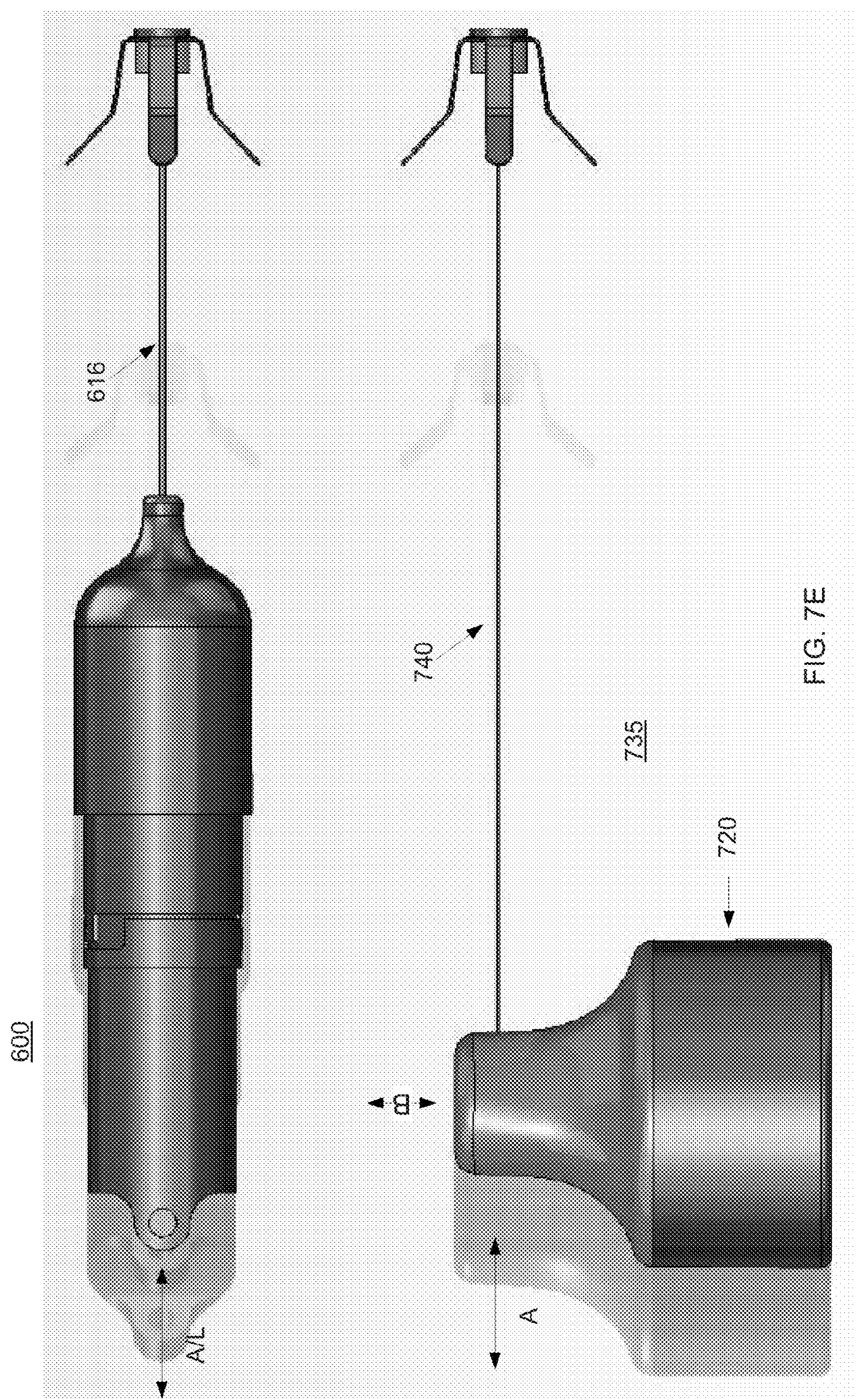
FIG. 7E is a side view comparing the operation of the tongue implant devices of FIG. 6A and FIG. 7C, according to embodiments of the invention.

FIG. 7E shows a comparative illustration between implants 600 and 735. Implant 735 includes implant housing 710 and linking section 740, which is configured similarly to the linking section 616 of implant 600. As described herein, the main longitudinal axis L of implant 600 is in the same approximate direction to the pulling axis A, which extends between the mandible and tongue. Conversely, the main longitudinal axis B of implant 735 operates in an approximate transverse direction to the pulling axis A, which extends between the mandible and tongue.

Figure 7F:
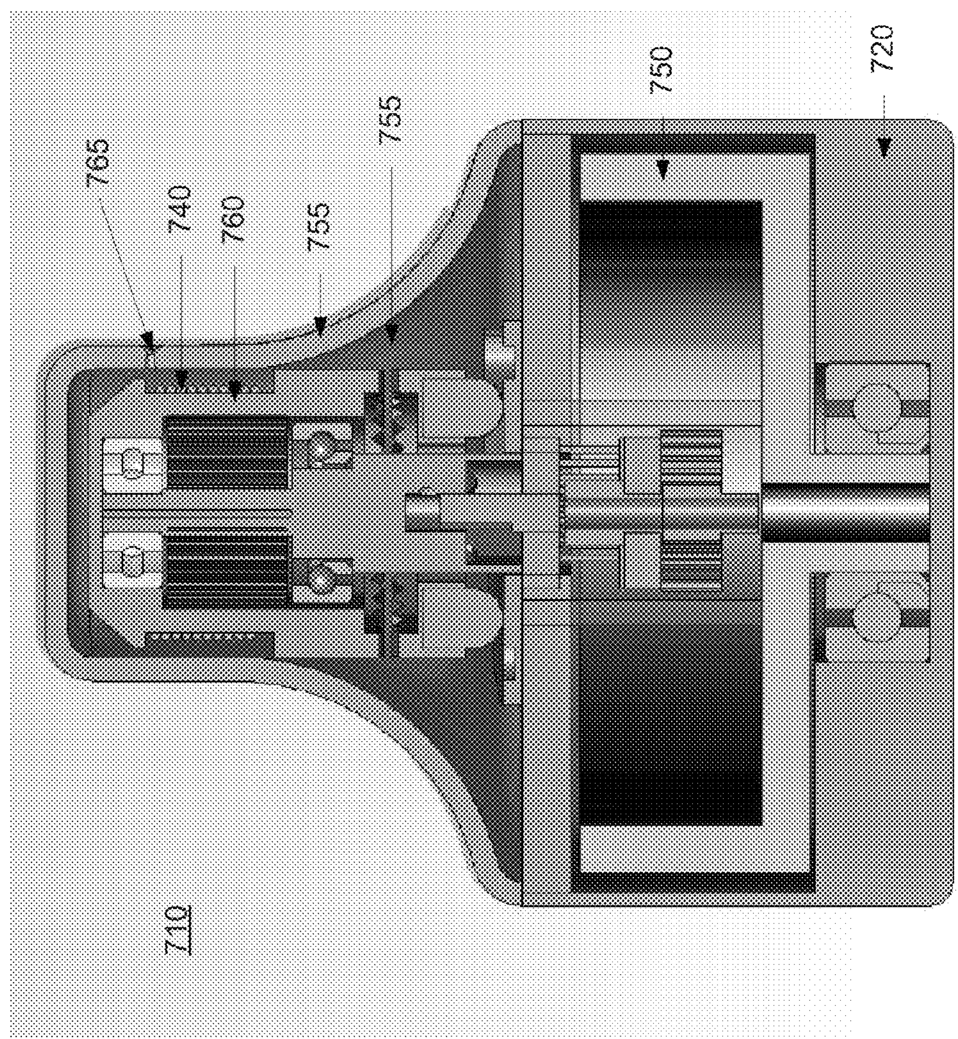
FIG. 7F is cross-sectional view of the tongue implant device of FIG. 7C.

FIG. 7F shows a cross-sectional view of implant housing 710, according to an embodiment of the invention. Implant housing 710 functions mechanically in the same general manner as discussed with reference to implant 600. The cylindrical base 720 houses a bearing supported rotor/gearbox assembly 750, which outputs to a tension relief mechanism 755, which in turn outputs to double bearing supported spool 760. The stator/gearbox assembly 750 may utilize a commercially available gear box having a 16:1 gear ratio. The linking section 740 spools around spool 760 for extension and retraction in and out of the upper cylindrical portion 725 via opening 765. In some embodiments, the opening 765 may be an elongated slit.

Figure 7G:
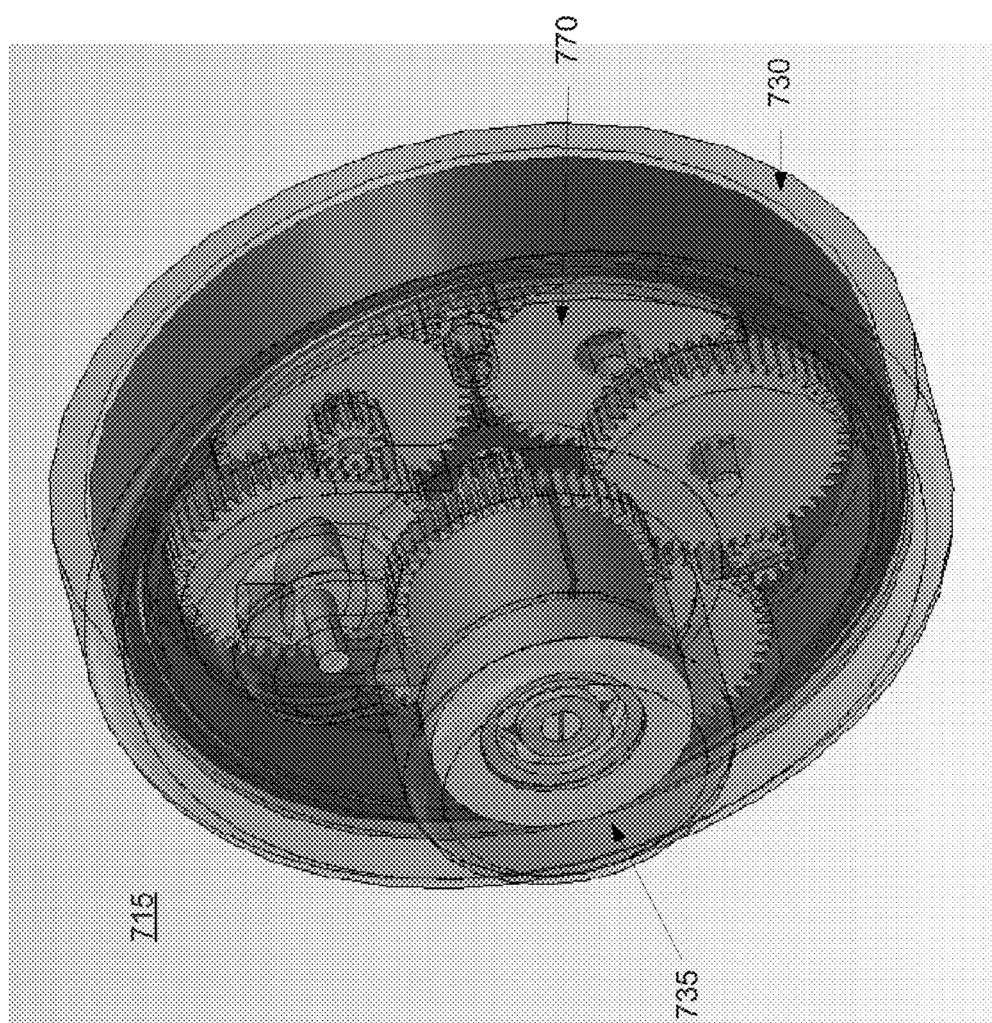
FIG. 7G is partially transparent perspective view of the tongue implant device of FIG. 7D.

FIG. 7G shows a partially transparent view of implant housing 715. Implant housing 715 functions mechanically in the same general manner as discussed with reference to implant 600. However, implant housing 715 utilizes a spur gear train 770. In some embodiments, the spur gear train can be configured to have a gear ratio ranging up to 256:1. The spur gear train 770 is arranged to make use of all the interior volume of the cylindrical base 730 by stacking gears along multiple parallel axis, and accordingly has a compact longitude profile.

Figure 8:
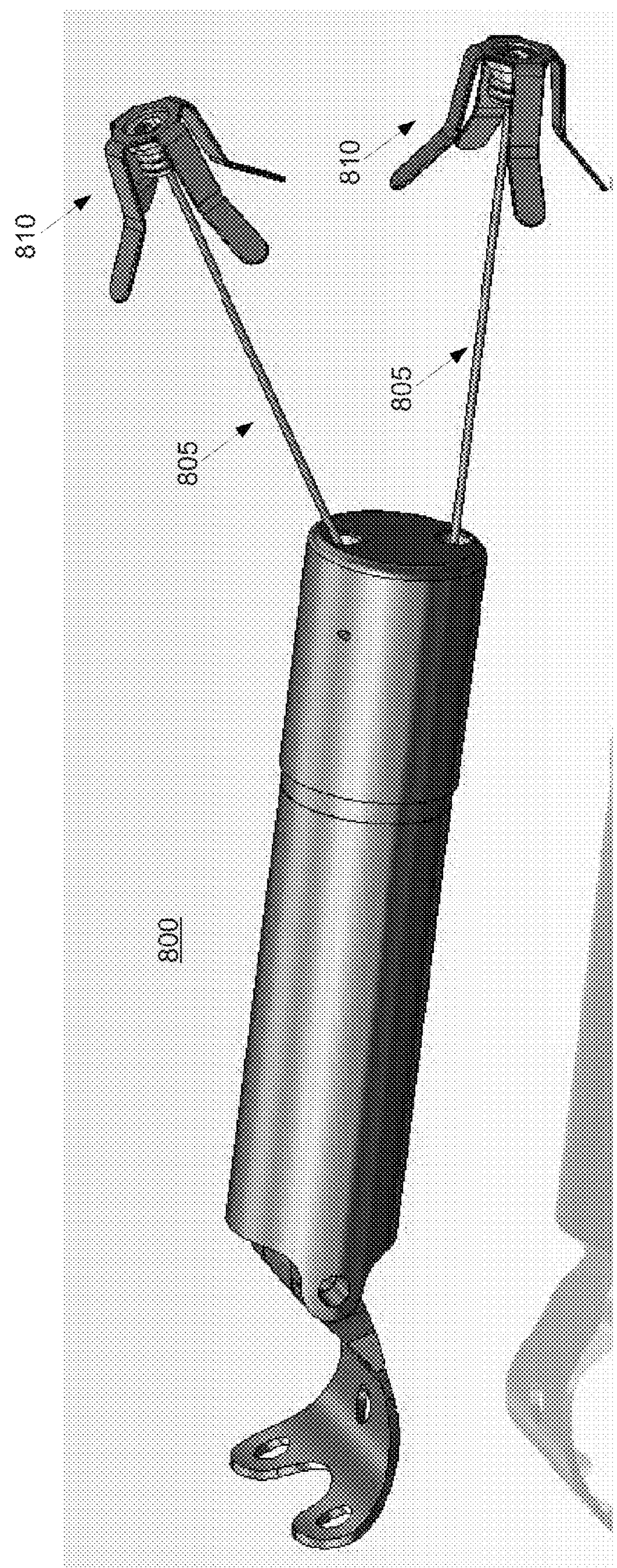
FIG. 8 is a perspective view of a tongue implant device, according to an embodiment of the invention.

FIG. 8 shows an implant 800, according to an embodiment of the invention. Implant 800 functions mechanically in the same general manner as described with reference to implant 600. However, implant 800 includes a plurality of linking sections 805 and respective tongue anchors 810. The linking sections 805 may spool around a single spool, or alternatively individual spools. Two linking sections 805 are shown, however, more may be used. Using a plurality of linking sections 805 and respective tongue anchors 810 may allow the tongue of a patient to be positioned closer to the mandible in a more efficient manner by providing a larger airway gap. The plurality of tongue anchors 810 also distributes the required force to manipulate the tongue over a wider area, resulting in a lower risk of anchor/tissue failure. It should be understood that all of the implant embodiments disclosed herein can implement a plurality of linking sections 805 and respective tongue anchors 810.

Figure 9A:
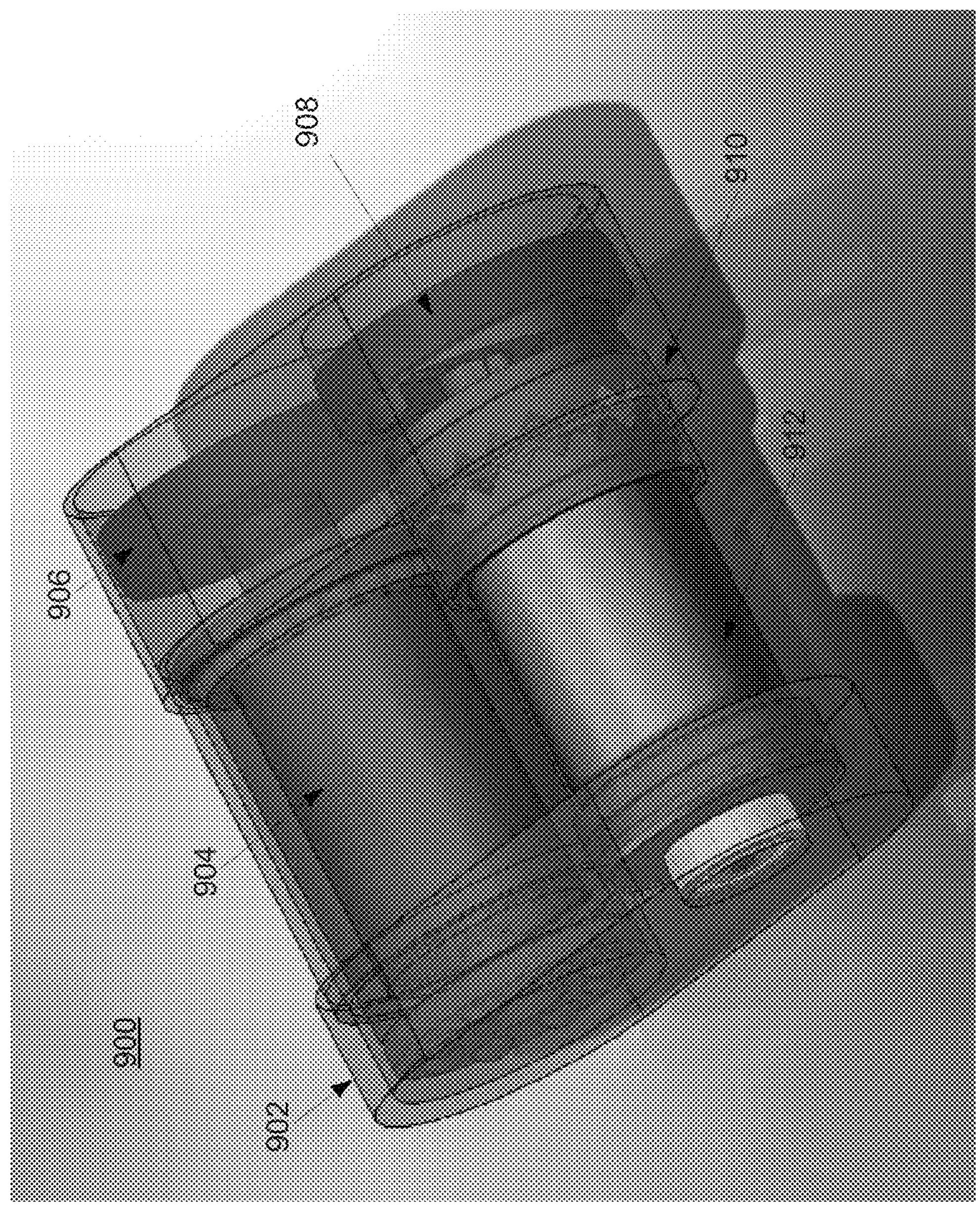
FIG. 9A is partially transparent perspective view of a tongue implant device, according to an embodiment of the invention.

FIG. 9A shows an implant 900 according to an embodiment of the invention. Implant 900 functions mechanically in the same general manner as described with reference to implant 600, however, implant 900 features a side-by-side power train arrangement. Implant 900 includes an elongated housing 902 with a oval or race track profile. One side of the housing 902 houses a rotor/gearbox assembly 904 which outputs to a first gear 906. A second gear 908 is coupled to the first gear 906 for transfer of power from the rotor/gearbox assembly 904 to a tension relief mechanism 910, which in turn outputs to a spool 912. The spool 912 is shown as fully exposed, but in some embodiments may be concealed within the housing 902. The first gear 906 and second gear 908 are shown to have a direct connection, but in some embodiments may have an indirect connection via a chain or belt. The first gear 906 and second gear 908 coupling may have a 1:1 or a different gear ratio.

Figure 9B:
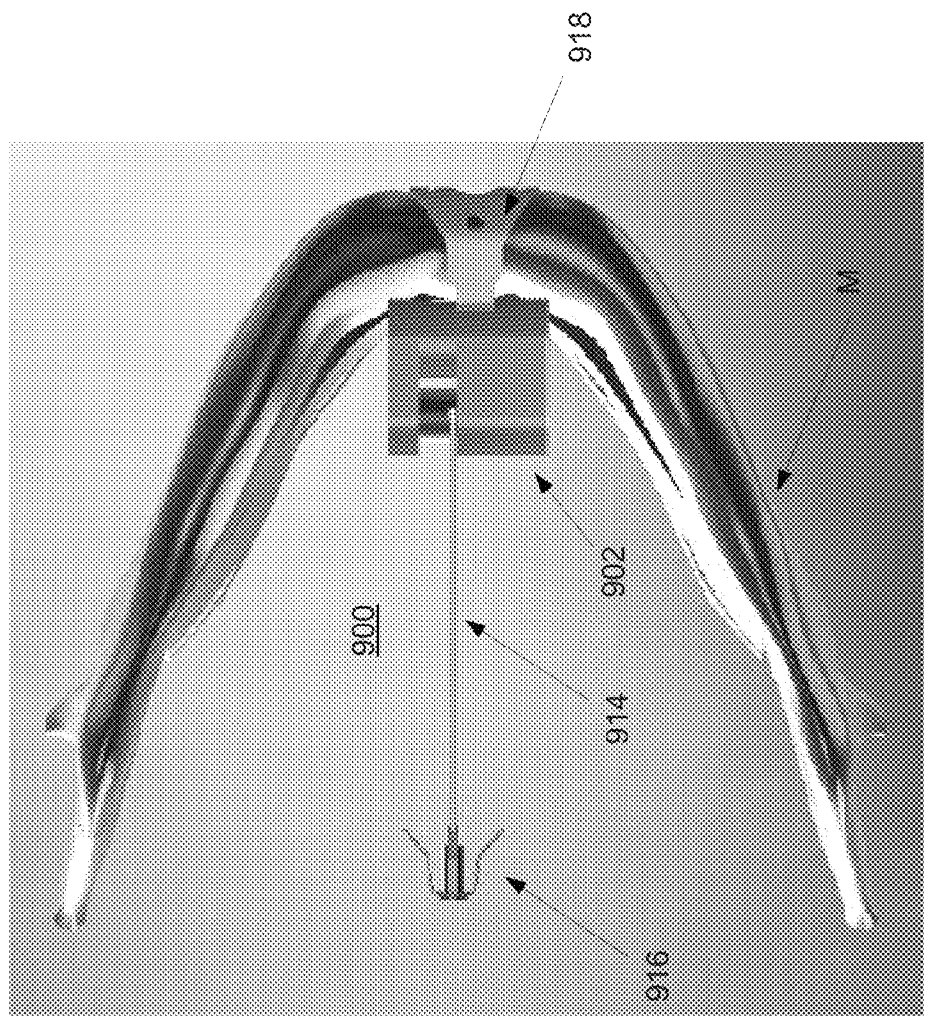
FIG. 9B is a perspective view of the tongue implant device of FIG. 9A in use, according to an embodiment of the invention.

FIG. 9B shows the implant 900 in use, according to an embodiment of the invention. The implant 900 is positioned such that the spool 912 is transversely arranged with respect to the pulling direction of linking section 914 and anchor 916. The housing 902 is connected to the mandible M via a mandibular anchor 918. The implant 900 provides compact layout which can occupy a minimal amount of longitudinal space and vertical height within the mandible M.

Figure 10A:
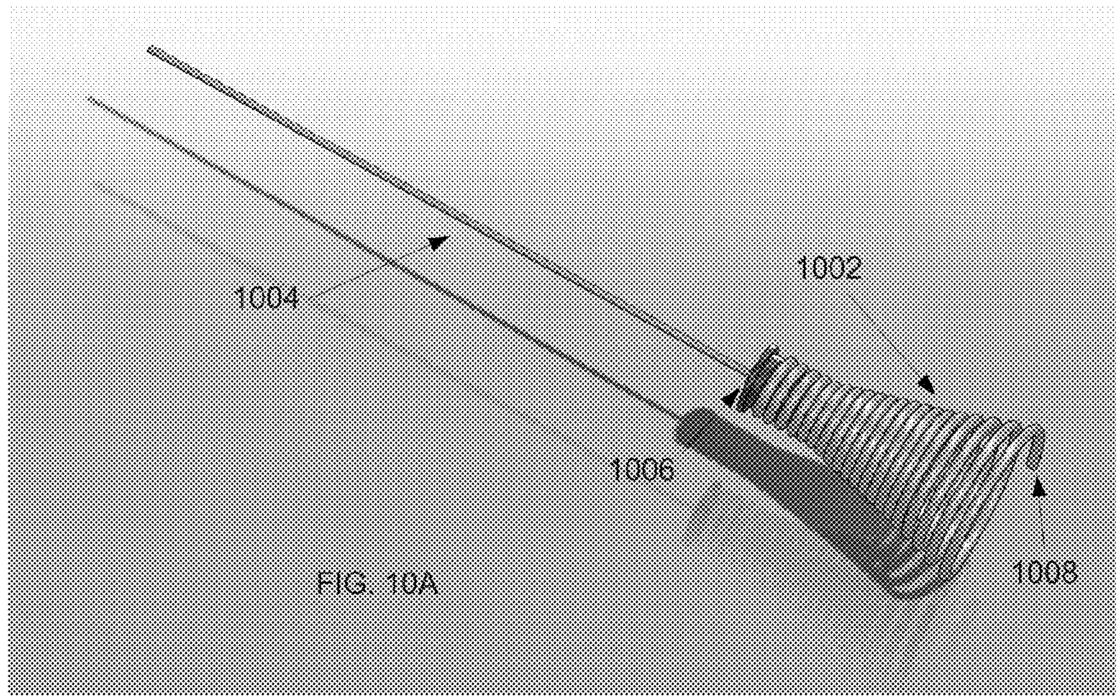
FIGS. 10A and 10B are perspective views of flexible anchors, according to embodiments of the invention.

FIG. 10A shows a flexible anchor 1002 for use with any of the implants described herein, according to an embodiment of the invention. The flexible anchor 1002 can resiliently elongate along an axis of a linking section 1004, which can connect to any of the implants described herein. In this embodiment the flexible anchor 1002 is configured as a tension spring that has a gradually increasing diameter in a proximal direction. Alternatively, this arrangement can be reversed such that the larger diameter is at a distal area closer to the linking section. Other spring configurations can be used, such as an hour-glass or inverse hour-glass. The flexible anchor 1002 can be constructed from a variety of resilient metals (e.g., stainless steel, titanium, NiTi), polymers, or metal/polymer combinations. The flexible anchor 1002 is connected to the linking section 1004, via a spring coupler 1006, which diametrically sized and configured to fix to an internal portion of the flexible anchor 1002 via an interference fit, welding, soldering, bonding, etc. The proximal-most end 1008 of the flexible anchor 1002 can have a sharpened tip configured to screw into the base of the tongue upon rotational movement of the flexible anchor 1002, and thus secure a portion of the flexible anchor 1002 into tissue.

The flexible anchor 1002 may be configured to partially elongate under a force which is less than the force that the threshold amount of force required to trigger a coupled-to tension relief mechanism, and fully elongate under a force which is greater than the force that the threshold amount of force required to trigger the coupled-to tension relief mechanism. Accordingly, movement of the tongue will cause the flexible anchor 1002 to partially elongate, however, the flexible anchor 1002 will not fully elongate before the tension relief mechanism is triggered. In other embodiments, the flexible anchor 1002 is configured to fully elongate under a force which is greater than the force that the threshold amount of force required to trigger the coupled-to tension relief mechanism. In these later embodiments, the flexible anchor is longitudinally arranged to have a fully elongated length which is relatively shorter than the distance between a base of the tongue and a coupled-to implant.

In use, the flexible anchor 1002 will provide resilient slack to the linking section by fully or partially elongating before a coupled-to tension relief mechanism is triggered. This slack provides more operational flexibility to the implants herein, as a tension relief mechanism can be configured to have a higher triggering force as compared to a mechanism without the flexible anchor 1002. The flexible anchor 1002 can compensate for quick jerking motions of the tongue which are not associated with a sleep apnea event, but would otherwise trigger an implant.

Figure 10B:
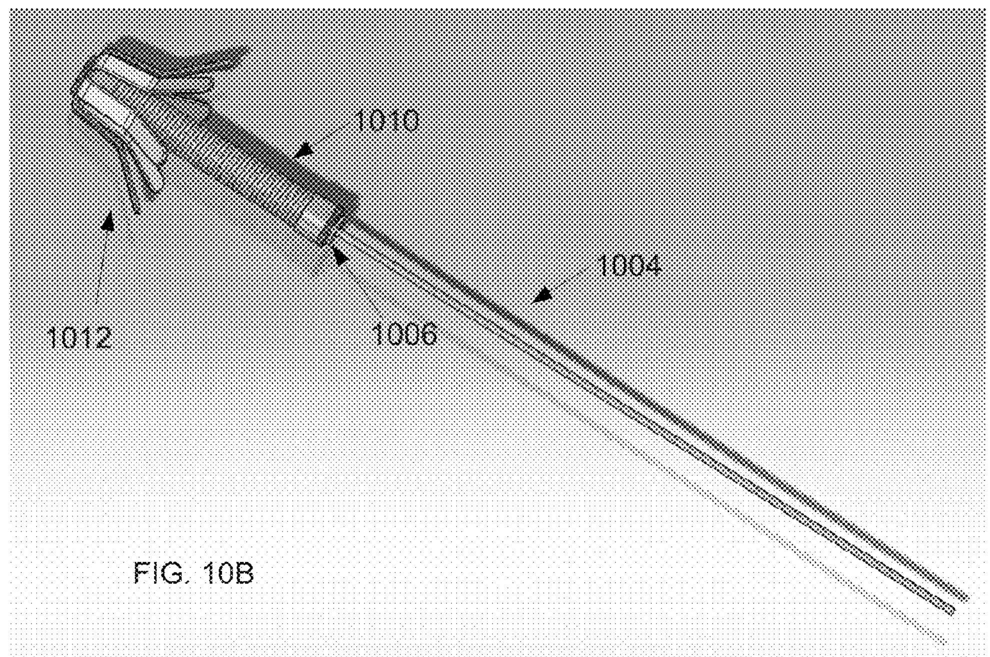

FIG. 10B shows a flexible anchor 1010 for use with any of the implants described herein, according to an embodiment of the invention. The flexible anchor 1010 is generally configured and used in the same manner as described with flexible anchor 1002. In this embodiment, the flexible anchor 1010 is configured as a tension spring with a uniform diameter. Accordingly, the flexible anchor 1010 is further attached to a plurality of resilient anchors that are configured to be surgically embedded into the base of the tongue, as similarly described in accordance to other anchoring embodiments disclosed herein.

As will be understood by those skilled in the art, the present invention may be embodied in other specific forms without departing from the essential characteristics thereof. For example, embodiments of the present invention can include an MRI compatible motor for use in a variety of medical applications. In one embodiment, the implanted rotor and non-implanted control device can control operation of a pump or similar device. Other embodiments of the present invention can be used to move body tissue other than the tongue (e.g., a lap-band type device). Those skilled in the art will recognize, or be able to ascertain using no more than routine experimentation, many equivalents to the specific embodiments of the invention described herein. Such equivalents are intended to be encompassed by the following claims.

What is claimed is:

1. An implantable device for stabilizing a tongue, comprising:

a mandibular anchor;

an actuator mechanism securable to the mandibular anchor, the actuator mechanism comprising a rotor having an output;

a gearbox coupled to the output of the rotor;

a tongue anchor which is anchorable to a base of the tongue;

a tension relief mechanism coupled to the gearbox;

a spool coupled to the tension relief mechanism; and a linking section coupled to the spool, the linking section joining the actuator mechanism to the tongue anchor, wherein the linking section is adapted to exert a pulling force on the tongue anchor in response to an operation of the actuator mechanism;

wherein the tension relief mechanism is configured to disengage the spool from the gearbox when a pulling force applied to the linking section exceeds a threshold value.

2. The implantable device of claim 1, wherein the tension relief mechanism comprises a spring.

3. The implantable device of claim 2, wherein the spring begins to elongate when a force between the mandibular anchor and the tongue anchor exceeds the threshold value.

4. The implantable device of claim 3, wherein the spring forms part of or is in series with the linking section between the actuator mechanism and the tongue anchor.

5. The implantable device of claim 3, wherein the spring is a closed coil spring.

6. The implantable device of claim 3, wherein the tension relief mechanism comprises a compression element captured between tension members.

7. The implantable device of claim 2, wherein the linking section is flexible in relation to a tension of the spring.

8. The implantable device of claim 1, wherein the rotor is coupled to a shaft, the shaft rotatable with rotation of the rotor, and wherein the pulling force on the tongue anchor is based on a rotation of the rotor.

9. The implantable device of claim 8, wherein the gearbox has an input coupled to the shaft and an output coupled to the linking section.

10. The implantable device of claim 9, wherein the gearbox comprises one of a planetary gearbox, spur gear train, work gear, hydraulic pump, pneumatic pump, friction clutch, screw mechanism, spring mechanism, compressed ball bearing mechanism, and pulley system adapted so as to provide the output at a reduced rotational speed relative to a rotational speed of the shaft.

11. The implantable device of claim 9, wherein the linking section comprises a tether coupled to the spool at one end and to the tongue anchor at another end.

12. The implantable device of claim 8, wherein the rotor is adapted to rotate under an influence of an electromagnetic field external to the implantable device.

13. The implantable device of claim 1, wherein the tongue anchor comprises a tension spring configured to partially or fully elongate when below the threshold value.

14. The implantable device of claim 13, wherein the tension spring is configured to screw into the base of the tongue.

15. The implantable device of claim 13, wherein the tension spring is connected to a plurality of resilient anchoring members.

16. The implantable device of claim 1, further comprising a second tongue anchor, wherein the linking section comprises a first tether and a second tether each coupled at one end to the actuator mechanism and to a respective one of the tongue anchors at another end.

17. The implantable device of 16, wherein a location of the second tongue anchor is different than a location of the tongue anchor.

18. The implantable device of claim 1, wherein the pulling force on the tongue anchor is less than 10 N and the threshold value is greater than 1 N.

19. The implantable device of claim 18, wherein the pulling force on the tongue anchor is in the range of 2-5 N and the threshold value is greater than 2 N.

20. The implantable device of claim 1, wherein the linking section comprises a rigid structure.

* * * * *